(12) United States Patent
Asrar et al.

(10) Patent No.: US 6,858,634 B2
(45) Date of Patent: Feb. 22, 2005

(54) CONTROLLED RELEASE FORMULATIONS AND METHODS FOR THEIR PRODUCTION AND USE

(75) Inventors: Jawed Asrar, Chesterfield, MO (US); James F. Essinger, Jr., Marysville, OH (US)

(73) Assignee: Monsanto Technology LLC, St. Louis, MO (US)

( * ) Notice: Subject to any disclaimer, the term of this patent is extended or adjusted under 35 U.S.C. 154(b) by 163 days.

(21) Appl. No.: 09/950,114

(22) Filed: Sep. 10, 2001

(65) Prior Publication Data

US 2002/0103086 A1 Aug. 1, 2002

Related U.S. Application Data

(60) Provisional application No. 60/232,693, filed on Sep. 15, 2000.

(51) Int. Cl.[7] .................... A01N 43/653; A01N 43/50; A01N 43/56; A01N 43/80; A01N 43/76
(52) U.S. Cl. .................. 514/372; 514/374; 514/381; 514/383; 514/385; 504/139; 504/272; 504/275; 504/280
(58) Field of Search ............................... 514/372, 374, 514/381, 383, 385; 504/139, 272, 275, 280

(56) References Cited

U.S. PATENT DOCUMENTS

| | | | |
|---|---|---|---|
| 3,523,906 A | 8/1970 | Hove et al. | 252/316 |
| 3,523,907 A | 8/1970 | Hove et al. | 252/316 |
| 4,007,258 A | 2/1977 | Cohen et al. | 424/22 |
| 4,282,209 A | 8/1981 | Tocker | 424/81 |
| 4,405,360 A | 9/1983 | Cardarelli | 71/117 |
| 4,554,155 A | 11/1985 | Allan et al. | 424/22 |
| 4,722,838 A | 2/1988 | Tocker | 424/81 |
| 4,818,534 A | 4/1989 | Levy | 424/404 |
| 4,849,415 A | 7/1989 | Zweigle | 514/89 |
| 4,983,389 A | 1/1991 | Levy | 424/404 |
| 4,983,390 A | 1/1991 | Levy | 424/404 |
| 4,985,251 A | 1/1991 | Levy | 424/404 |
| 4,990,335 A | 2/1991 | Bateman et al. | 424/408 |
| 5,129,180 A | 7/1992 | Stewart | 47/57.6 |
| 5,567,430 A | 10/1996 | Levy | 424/409 |
| 5,580,573 A * | 12/1996 | Kydonieus et al. | 424/449 |
| 5,639,476 A | 6/1997 | Oshlack et al. | 424/468 |
| 5,698,210 A | 12/1997 | Levy | 424/406 |
| 5,750,130 A | 5/1998 | Ferrell et al. | 424/417 |
| 5,824,328 A | 10/1998 | Levy | 424/409 |
| 5,846,553 A | 12/1998 | Levy | 424/409 |
| 5,849,433 A * | 12/1998 | Venugopal et al. | 429/303 |
| 5,858,384 A | 1/1999 | Levy | 424/406 |
| 5,858,386 A | 1/1999 | Levy | 424/409 |
| 5,876,739 A | 3/1999 | Turnblad et al. | 424/408 |
| 5,885,605 A | 3/1999 | Levy | 424/405 |
| 5,902,596 A | 5/1999 | Levy | 424/405 |
| 5,939,356 A | 8/1999 | Wellinghoff | 504/100 |
| 6,001,382 A | 12/1999 | Levy | 424/405 |
| 6,335,027 B1 | 1/2002 | Levy | 424/409 |
| 6,337,078 B1 | 1/2002 | Levy | 424/406 |
| 6,346,262 B1 | 2/2002 | Levy | 424/408 |
| 6,350,461 B1 | 2/2002 | Levy | 424/409 |
| 6,387,386 B1 | 5/2002 | Levy | 424/408 |
| 6,391,328 B1 | 5/2002 | Levy | 424/406 |

FOREIGN PATENT DOCUMENTS

| | | | | |
|---|---|---|---|---|
| DD | 291332 | * | 6/1991 | |
| EP | 0064379 | | 11/1982 | .......... A01N/25/10 |
| FR | 1568198 | | 3/1968 | |
| WO | WO 99/21419 | | 5/1999 | .......... A01N/25/34 |
| WO | 9927910 | * | 6/1999 | |
| WO | WO 99/27910 | | 6/1999 | ............ A61K/9/16 |
| WO | WO 99/00013 | | 7/1999 | |

OTHER PUBLICATIONS

McFarlane et al., *Pesticide Science*, 9:411–424 (1978); in *Controlled Delivery of Crop–Protection Agents*, R.M. Wilkins, Ed., Taylor & Francis, London (1990).
Sparks et al., in *Selection of Coating and Microencapsulation Processes*, pp. 3–29, in *Controlled Release Delivery Systems for Pesticides*, H.B. Scher, Ed., Marcel Dekker, Inc., New York, 1999.
Sliwka, W., *Angew. Chem. internat. Edit.* 14:539–550 (1975).
Thies, C. at pp. 628–651 of vol. 16, of *Kirk–Othmer Encyclopedia of Chemical Technology*, Fourth Ed., John Wiley & Sons, New York (1995).
Finch, C.A., in *Chemistry and Industry*, pp. 752–756, Nov. 18 (1985).
Bahadir, M. et al., *Controlled Release of Pesticides*, pp. 1–64 in *Controlled Release, Biochemical Effects of Pesticides, Inhibition of Plant Pathogenic Fungi: Chemistry of Plant Protection 6*, Bowers, W.S. et al., Eds., Springer–Verlag, Berlin (1990).
Park et al., in *Controlled Release of Pesticides from Microparticles*, pp. 89–136, in *Controlled Release Delivery Systems for Pesticides*, H.B. Scher, Ed., Marcel Dekker, Inc., New York, 1999.
Smith, in *Dispersible Microparticles*, pp. 137–149, of *Controlled Release Delivery Systems for Pesticides*, H.B. Scher, Ed., Marcel Dekker, Inc., New York, 1999.
Wilkins, R.M. in *Controlled Release Rate Methods, with Emphasis on Lignin–Based Methods*, pp. 195–222 of *Controlled Release Delivery Systems for Pesticides*, H.B. Scher, Ed., Marcel Dekker, Inc., New York, 1999.
International Search Report for Application No. PCT/US01/28531 dated Jun. 13, 2002.

* cited by examiner

Primary Examiner—Alton Pryor
(74) Attorney, Agent, or Firm—Nelson Mullins Riley Scarborough, LLP

(57) ABSTRACT

Controlled release formulations for pesticides and herbicides contain an active ingredient, a matrix polymer and a matrix polymer plasticizer which is present in an amount sufficient to provide a release rate for the active ingredient from the formulation that matches a selected release rate. Methods for making and using the formulation, and seeds and plants that have been treated with the formulations are also included.

61 Claims, 10 Drawing Sheets

CONTROLLED RELEASE FORMULATIONS AND METHODS FOR THEIR PRODUCTION AND USE

This Application claims the benefit of U.S. Provisional Application No. 60/232,693, filed Sep. 15, 2000.

FIELD OF THE INVENTION

The present invention relates to the production and use of formulations for the controlled release of active ingredients, and more particularly to the production and use of controlled release formulations for which the release rate of the active ingredient can be regulated to match a desired release rate.

DESCRIPTION OF THE RELATED ART

Controlled release formulations have found commercial utility in medicine, printing and copying applications, cosmetics, paints and coatings, and many other fields. Agricultural uses of controlled release products have also begun to become important, but thus far, most commercial agricultural controlled release products are relatively simple granules or capsules that degrade slowly in an application environment and thereby release fertilizers or other active ingredients.

The use of pesticides is a widespread practice that has become an integral part of modem agriculture. The ability to control insect damage to crops and to limit the deleterious effects of weeds and other plant pests has increased modem crop yields to many times that of pre-pesticide agriculture.

Most pesticides are applied to soil or directly to growing plants. But these application methods have sometimes resulted in problems with runoff, evaporation, and contamination of surface waters with pesticides; with inefficient targeting of the pesticide to the point of its effect; and with unacceptable exposure of farmers, applicators, and nearby residents to the pesticides. Such problems have resulted in, at least, the inefficient use of the pesticides, and, worse, have caused significant environmental degradation and human and animal sickness and even death.

One response to problems of this sort has been the development and use of controlled release pesticide products. General information on types of controlled release pesticides, and methods for their production can be found in, for example, McFarlane et al., *Pesticide Science*, 9:411–424 (1978); in *Controlled Delivery of Crop-Protection Agents*, R. M. Wilkins, Ed., Taylor & Francis, London (1990); and *Controlled-Release Delivery Systems for Pesticides*, H. B. Scher, Ed., Marcel Dekker, Inc., New York, (1999).

As used herein, a "controlled release pesticide" is a composition that includes at least one pesticide and is capable of releasing the pesticide into the application environment at a lower rate than the pesticide would be released if applied without being included in the composition. The "application environment" is the environment immediately surrounding the pesticide composition in which it is desired that the pesticide demonstrate its pesticidal effect. This is normally the environment in which the controlled release pesticide would be expected to encounter the pest that it is designed to control.

Many forms of controlled release products have been reported. For example, microcapsules are small pesticide-containing liquid droplets or solid particles that are enclosed by a coating that controls the transport of the pesticide from the droplet or particle into the application environment. Microcapsules can be formed by many different processes, several of which have been described by Sparks et al., in *Selection of Coating and Microencapsulation Processes*, pp. 3–29, in *Controlled Release Delivery Systems for Pesticides*, H. B. Scher, Ed., Marcel Dekker, Inc., New York, 1999; by Sliwka, W., *Angew. Chem. internat. Edit.* 14:539–550 (1975); and by Thies, C. at pp. 628–651 of Vol. 16, of *Kirk-Othmer Encyclopedia of Chemical Technology*, Fourth Ed., John Wiley & Sons, New York (1995). Finch, C. A., in *Chemistry and Industry*, pp: 752–756, Nov. 18 (1985), describes a number of polymers that can be used for the walls of microcapsules, but does not discuss their use with pesticides. Tocker, in U.S. Pat. No. 4,722,838, describes self-microencapsulating controlled release pesticidal compositions consisting essentially of a barrier polymer, a pesticidal agent, and at least one surfactant, all of which are dissolved in an organic solvent, and which form microcapsules when the solution is added to water with mild agitation. Microparticles were made with the pesticides methomyl, oxamyl, and sulfonylurea with polymethylmethacrylate barrier polymer. In U.S. Pat. No. 4,282,209, Tocker described a process for preparing insecticide-polymer particles for the controlled release of methomyl that also utilized poly(methylmethcrylate) as the barrier polymer.

Matrix microparticles are typically small solid particles in which an active ingredient—one or more pesticides—is dispersed throughout a matrix material. The mathematics of release of actives from matrix systems has been discussed in general by Bahadir, M. et al., *Controlled Release of Pesticides*, pp. 1–64 in *Controlled Release, Biochemical Effects of Pesticides, Inhibition of Plant Pathogenic Fungi: Chemistry of Plant Protection* 6, Bowers, W. S. et al., Eds., Springer-Verlag, Berlin (1990).

Different types of matrix microparticles are described by Park et al., in *Controlled Release of Pesticides from Microparticles*, pp. 89–136, in *Controlled Release Delivery Systems for Pesticides*, H. B. Scher, Ed., Marcel Dekker, Inc., New York, 1999. In this reference Park et al. recognized that the choice of microparticle, system and matrix must be tailored to the physical and chemical properties and to the mode of action of individual active compounds. In particular, the reference focused on the production of microparticles having trifluralin, chlorpyrofos and atrazine as active ingredients. Several rosins, waxes, and synthetic polymers were tested as matrix materials for these three pesticides, and examples of other actives mixed with lignins, cyclodextrins, flours and starches were mentioned.

Smith, in *Dispersible Microparticles*, pp. 137–149, of *Controlled Release Delivery Systems for Pesticides*, H. B. Scher, Ed., Marcel Dekker, Inc., New York, 1999, describes several different types of matrix microparticles and discusses the effect of particle size on interparticle spacing after application. Particles having a size range between 20 microns and 100 microns were recommended.

Another consideration regarding the size of matrix microparticles is its effect upon the release rate of the active. Wilkins, R. M. in *Controlled Release Rate Methods, with Emphasis on Lignin-Based Methods*, pp. 195–222 of *Controlled Release Delivery Systems for Pesticides*, H. B. Scher, Ed., Marcel Dekker, Inc., New York, 1999, stated that molten alkali lignin is plasticized by some pesticides, and that when the lignin and the active are compatible, they will form a glassy matrix upon cooling, which can be ground to produce small particles. The reference discloses that the compatibility range of a lignin and a pesticide can be assessed by observing a film of the (solidified) melt mixture under a microscope for the presence of unsolvated lignin partices. It also suggests that where solvation does occur, the melting point of the pesticide is depressed. A melting point depression is shown for diuron and ametryn, but not for trifluralin, in mixtures with pine Kraft lignin. The release rate of imidacloprid (which was reported to be a good plasticizer for lignin) from organosolv lignin granules was shown to be a function of particle size for relatively large particles from about 1.0 mm in diameter down to under about 0.25 mm (about 250 microns). In general, the smaller the particle, the faster the release rate of the pesticide. The reference did not show how significantly smaller microparticles of imidacloprid and lignin could be made, nor how the release rate could be controlled in such small particles.

Very small particle size is advantageous when pesticidal matrix microparticles are to be applied by spray, since such small particles do not clog the spray equipment and can be distributed evenly upon the target seed or plant. Moreover, very small particles, i.e., under about 100 microns, function well in seed coatings since they adhere better than do larger particles. However, the release rate of a pesticide from such small particles is often so rapid that any benefit from the use of the microparticles is lost. This can be illustrated by the fate of a seed coating that contains a pesticide, such as a fungicide, that is targeted to protect not only the seed, but also the future plant during sprouting and emergence. Since it can take a seed from one to two weeks to sprout after planting, and protection is then needed for several more weeks, it is critical that an effective amount of the pesticide remain available to protect the plant throughout this period. If most of the pesticide has been released from the microparticles before the seed has sprouted, there is a good chance that it could be leached away, or evaporate, before its pesticidal activity is needed. Thus, the pesticide could be wasted without providing the desired protection. Accordingly, it would advantageous to be able to provide pesticidal matrix microparticles, especially very small particles, for which the release rate could be matched to a desired rate.

Another important characteristic of pesticidal matrix microparticles is that they incorporate a large percentage, and preferably almost all, of the active pesticide within the particles—rather than on the surface of the particles or in crystals of the pesticide that are external to the microparticles. Such external pesticide is easily leached away from the point of application, and does not benefit from the controlled release feature. It is known that chemical and physical properties of the pesticide and the matrix polymer can affect this characteristic. Moreover, it is believed that the chemical and physical properties of the active and the matrix polymer, along with the size of the particles, can affect the performance of the microparticles—e.g., the release profile of the active; the loading amount of active; the stability of the active in the formulation; and the like. Since the chemical and physical properties of various pesticides differ significantly, it would be expected that no one technique or formulation would be successful for all pesticides. Accordingly, it has been difficult to predict that any particular method of forming a matrix microparticle would work for any combination of active and matrix material, or that any one particular matrix formulation would work successfully with all types of pesticides.

Effective controlled release formulations are not known to be reported for some pesticides, notably fungicides, and in particular, azoles such as tebuconazole. Nonetheless, certain of these chemicals have very desirable pesticidal activities and it would be useful to be able to produce controlled release formulations that permitted safer and more efficient use of the pesticides. In particular, it would be advantageous to provide methods for the production of controlled release formulations of such azoles as tebuconazole, which resulted in the incorporation of all, or a majority of, the pesticide into the formulation. Furthermore, it would be advantageous if these controlled release formulations could be made to demonstrate desirable release rate profiles and be suitable for easy spray application and for use as a seed coating.

SUMMARY OF THE INVENTION

Briefly, therefore, the present invention is directed to a novel formulation for the controlled release of an active ingredient comprising an active ingredient dispersed in a matrix polymer that has a reduced glass transition temperature when intermixed with the active ingredient; and a matrix polymer plasticizer; also to a novel controlled release formulation comprising tebuconazole in an amount of about 30% to 40% by weight, and poly(methyl methacylate) and phthalic anhydride or poly(vinyl acetate) in a weight ratio of from about 90:10 to 50:50; also to a novel controlled release formulation comprising tebuconazole in an amount of about 30% to 40% by weight, and poly(styrene-co-maleic anhydride) and poly(vinyl acetate) in a weight ratio of from about 90:10 to 50:50; also to a novel method of making a formulation for the controlled release of an active ingredient comprising intermixing an active ingredient and a matrix polymer with a sufficient amount of a matrix polymer plasticizer to provide a formulation having a release rate for the active ingredient that matches a selected release rate; also to a novel method of administering an active ingredient to seeds by treating the seeds with a controlled release formulation comprising an active ingredient dispersed in a matrix polymer that has a reduced glass transition temperature when intermixed with the active ingredient; and a matrix polymer plasticizer; also to a novel method of administering a pesticide to a plant by treating the plant with a controlled release formulation comprising an active ingredient dispersed in a matrix polymer that has a reduced glass transition temperature when intermixed with the active ingredient; and a matrix polymer plasticizer; also to a novel seed that has been treated with a controlled release formulation comprising an active ingredient dispersed in a matrix polymer that has a reduced glass transition temperature when intermixed with the active ingredient; and a matrix polymer plasticizer; also to a novel plant that has been treated with a controlled release formulation comprising an active ingredient dispersed in a matrix polymer that has a reduced glass transition temperature when intermixed with the active ingredient; and a matrix polymer plasticizer.

Among the several advantages found to be achieved by the present invention, therefore, may be noted the provision of a formulation for the controlled release of an active ingredient where the release rate of the active ingredient from the formulation can be regulated to be matched to a selected release rate when the formulation is in the application environment; the provision of such formulation that can be provided in a form that adheres well to a seed; and the provision of such a formulation that has a low level of readily extractable active ingredient.

BRIEF DESCRIPTION OF THE DRAWINGS

FIG. 1 is a depiction of plant fresh weight as a function of time shown with illustrations of effective and toxic limits of a pesticide or herbicide and also illustrating the release of a pesticide or herbicide from active ingredient alone (AI ALONE), and from a controlled release formulation at a rate that is: ("A") so high as to be toxic, ("B") too low to be effective, and ("C") effective, non-toxic, and matched with the selected release rate;

FIG. 2 shows a photomicrograph of microparticles of a controlled release formulation of the present invention in which tebuconazole is the active ingredient, poly(methyl metacrylate) is the matrix polymer and dibutyl phthalate is the matrix polymer plasticizer, showing the size and shape of the microparticles;

FIG. 3 shows the release rate of tebuconazole into water from matrix microparticles having 40% by weight loading of tebuconazole, with poly(methyl methacrylate) (PMMA) as the matrix polymer and polyvinyl acetate (PVA) as a plasticizer at levels ranging from zero to 70:30 (as a weight ratio of PMMA:PVA); and illustrates the effect that varying the level of plasticizer has on the release rate of the active;

Figure 6:
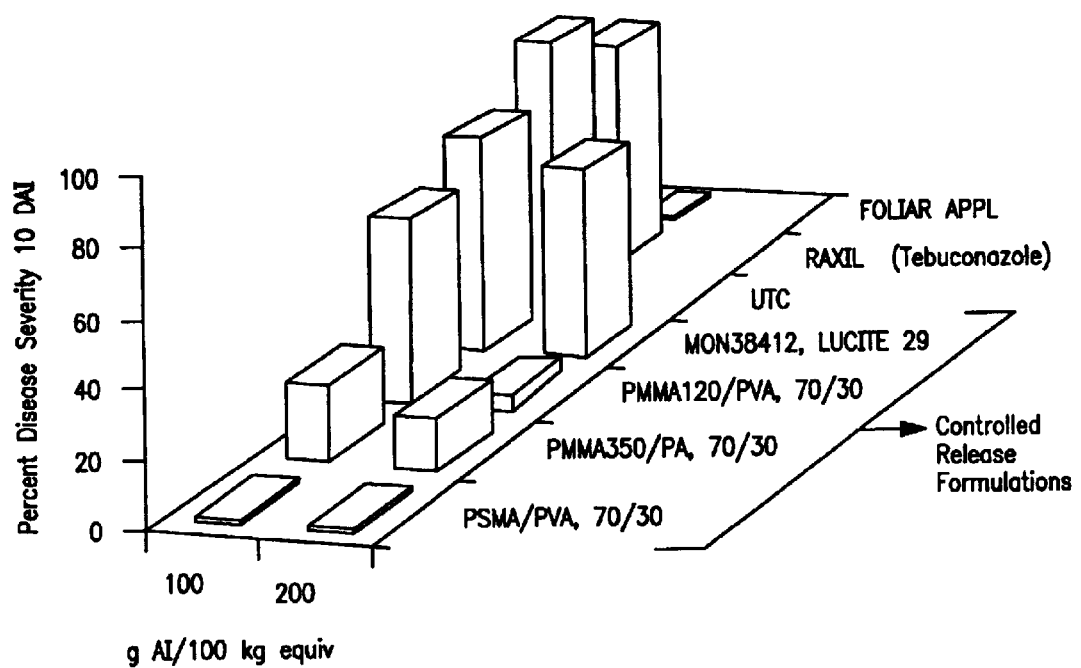

FIG. 6 shows disease severity of wheat rust on wheat third leaf 10 days after infestation and 28 days after injecting the soil surrounding the seed with three different controlled release formulations of the present invention that contained tebuconazole at two different levels, as compared with untreated wheat (UTC), wheat treated with matrix polymer and plasticizer without active ingredient (MON38412, LUCITE 29), and a commercial pesticide injected into the soil (RAXIL), or applied to the foliage (FOLIAR APPL); and FIG. 7 shows temperature schedules and plots of heat flow as a function of temperature for differential scanning calorimetry analysis of (a) poly(methyl methacrylate) (120,000 weight average molecular weight); (b) phthalic anhydride; (c) a 70/30 wt/wt blend of poly(methyl methacrylate) and phthalic anhydride; and (d) a 42/18/40 wt/wt/wt blend of poly(methyl metacrylate)/ phthalic anhydride/ and tebuconazole.

DETAILED DESCRIPTION OF THE INVENTION

In accordance with the present invention, it has been discovered that formulations for the controlled release of active ingredients, such as pesticides, herbicides and other biologically-active molecules, can be prepared by mixing the active with a matrix polymer and a selected amount of a matrix polymer plasticizer. By the selection of a matrix polymer that has a reduced glass transition temperature when mixed with the active ingredient; the selection of a matrix polymer plasticizer that is totally or partially miscible with the matrix polymer and has a plasticizing effect on the matrix polymer; and the inclusion of a certain amount of the plasticizer, the rate of release of the active ingredient from the formulation can be altered and even tailored to match to a pre-selected release rate.

The subject formulations protect seed and plants from phytotoxic pesticides, especially during the critical germination, sprouting, and early growth periods, and they permit more efficient pesticide use, because the release rate for the pesticide can be tailored to provide an effective amount of the pesticide at the time when it is needed. The formulations therefore reduce excess pesticide use and so also protect operators and users from harmful active ingredients, and protect the environment from excess pesticide loss/runoff. The formulations help preserve the activity of active ingredients during manufacture, storage, distribution and application. Moreover, when the formulations are used as seed treatments, the pre-treated seed requires no additional pesticide application step prior to, during, or soon after planting.

The subject controlled release formulations contain at least one active ingredient, a matrix polymer, and a plasticizer. These components will now be described in detail.

Active Ingredient

The formulations of the present invention contain an active ingredient. As used herein, the terms "active ingredient" mean any chemical element, molecule, or compound, or mixture thereof, which has a biological activity. Such active ingredients include, but are not limited to, pesticides, herbicides, plant growth regulators, drugs, dyes, biological attractants, scents and pheromones.

The subject formulations have been found to be especially useful when pesticides, plant growth regulators, or herbicides are the active ingredient. Examples of pesticides that can be used as active materials in the present invention are acaricides, miticides, insecticides, insect repellants, fungicides, fungistats, molluscicides, rodenticides, nematicides, bacteriacides, or an adjuvant for one or more of these.

It is known that many of the most useful pesticides, herbicides and plant growth regulators can be phytotoxic if they are allowed to contact plants or seeds in high concentrations. Consequently, it has been particularly difficult to supply these phytotoxic actives in concentrated form, such as in controlled release granules, coatings, or pellets, due to the harmful effect that the active can have upon the very seed or plant that it is designed to protect. An important property of the present formulations is that they permit the use of highly effective actives that are also phytotoxic. Without being bound to this or any other theory, it is believed that the subject formulations provide this property because they permit the release rate of the active ingredient to be selected and controlled so that the concentration of the active in contact with the seed or plant reaches levels that are effective to provide the protective feature of the active, while being sufficiently low to avoid phytotoxic damage to the seed or plant.

As used herein, a pesticide, herbicide, or plant growth regulator is "phytotoxic" if it causes any harm or damage whatsoever to the plant or seed it is being use to protect when it contacts that plant or seed at a concentration that is conventionally known or used in the trade to provide such protection. Plant and seed damage or harm includes, for example, stunting, chemical burning, yield depression, malformation, discoloration, lack of germination, death, and the like.

A preferred use for the subject formulations is to provide controlled release of fungicides, and particularly azole fungicides. Such azoles have been shown to be effective for protecting seeds and plants from damage by fungus, but some azole fungicides are phytotoxic. It is more preferred when the azole fungicide is selected from the group consisting of azaconazole, BAS 480F (epoxiconazole), biternatol, bromuconazole, cyproconazole, difenoconazole, diniconazole, fenbuconazole, fluquinconazole, flusilazole, flutriafol, hexaconazole, imazalil, imibenconazole, ipconazole, metconazole, myclobutanil, paclobutrazol, perfuazoate, penconazole, prochloraz, propiconazole, tebuconazole, tetraconazole, triadimefon, triadimenol, triflumizole, triticonazole and uniconazole. It is also preferred that the azole fungicide is one that is soluble in water at 20° C. in an amount of less than about 10 g/l.

A particularly preferred azole fungicide is tebuconazole.

The subject formulations have also been found to be preferred for the provision of controlled release of fungistats, and in particular, of N-Allyl-4,5-dimethyl-2-trimethylsilylthiophene-3-carboxamide.

Matrix Polymer

In the present formulations, the active ingredient is dispersed in a matrix polymer. The matrix polymer is selected to have a certain degree of physical and chemical compatibility with the active ingredient. It is believed that a matrix polymer having too high a compatibility with an active ingredient will result in a formulation that is easily made and has low REA, but which will provide an unacceptably slow release rate. On the other hand, when the compatibility of the matrix polymer and the active ingredient is too low, it will be difficult, or impossible to produce a controlled release microparticle, for example, and the REA will be unacceptably high. Since neither of these extremes would provide a valuable commercial product, it is believed to be preferred to match the chemical and physical compatibility of the matrix polymer and the active in a manner that will be discussed below.

It is preferred that the matrix polymer has a reduced glass transition temperature ($T_g$) when mixed with the active ingredient. Such mixing between the matrix polymer and the active can be done either in a melt of the two components, or by placing both components in a common solution. When it is said that the $T_g$ of the matrix polymer is reduced upon mixing with the active ingredient, what is meant is that $T_g$ of the matrix polymer is reduced by at least 1° C., preferably by at least 5.0° C., more preferably at least 10° C., and even more preferably by at least about 25° C., when the matrix polymer is intimately intermixed with 25% wt/wt of the active ingredient.

It is also preferred that the matrix polymer is one that is soluble in an organic solvent in which the active ingredient is also soluble. It is also preferred that the matrix polymer is not soluble in water, so that it does not dissolve in an application environment where it is contact with water. And it is preferred that the matrix polymer be a solid at 25° C. As used herein, the "organic solvent" in which the matrix polymer and the active ingredient are soluble can be any organic solvent in which both the matrix polymer and the active ingredient are soluble at room temperature in an amount of at least about 1 g/liter. It is preferred that both the matrix polymer and the active ingredient are soluble in the organic solvent in an amount of at least about 5 g/liter, but at least 10 g/liter is more preferred, at least about 25 g/liter is yet more preferred, and at least about 50 g/liter is even more preferred. When it is said that the matrix polymer is not soluble in water, it is meant that the water solubility of the matrix polymer at 25° C. is less than about 1% by weight. It is more preferred that the water solubility of the matrix polymer at 25° C. is less than about 100 ppm by weight.

When the subject formulation is being produced by an emulsion process, as described below, it is preferred that the organic solvent be one that is more volatile that the active ingredient. It is more preferred that the organic solvent has a normal boiling point of under about 200° C., and under about 150° C. is more preferred, under about 100° C. is even more preferred, and under about 50° C. is yet more preferred. When the matrix polymer is poly(methyl methacrylate) and the active ingredient is tebuconazole, for example, methylene chloride is a preferred organic solvent.

The present formulation can also be produced from a molten mixture, and for these processes, it is preferred that the matrix polymer has a normal melting temperature that is not more than 25° C. more than the normal melting point of the active ingredient. It is more preferred that the melting point of the matrix polymer be equal to or less than the decomposition temperature of the active ingredient. It is also preferred that the matrix polymer is totally or partially miscible with the active ingredient in a molten mixture of the matrix polymer and the active ingredient. Some useful matrix polymers can be amorphous polymers and have no $T_g$, or have a very poorly defined $T_g$. In those cases, it is preferred that the amorphous matrix polymer be one that is capable of being intermixed with the active ingredient into a formulation at a temperature that is below the decomposition temperature of the active ingredient.

Polymers that are suitable for use as the matrix polymer in the present invention can be polyesters, polycarbonates, co-polymers of styrene, and mixtures thereof. Examples of preferred matrix polymers are acrylonitrile-butadiene-styrene terpolymer (ABS); ABS modified polyvinylchloride; ABS-polycarbonate blends; acrylic resins and co-polymers: poly(methacrylate), poly(ethylmethacrylate), poly(methylmethacrylate), methylmethacrylate or ethylmethacrylate copolymers with other unsaturated monomers; casein; cellulosic polymers: ethyl cellulose, cellulose acetate, cellulose acetatebutyrate; ethyl vinyl acetate polymers and copolymers; poly(ethylene glycol); poly(vinylpyrrolidone); acetylated mono-, di-, and tri-glycerides; poly(phosphazene); chlorinated natural rubber; polybutadiene; polyurethane; vinylidene chloride polymers and copolymers; styrene-butadiene copolymers; styrene-acrylic copolymers; alkylvinylether polymers and copolymers; cellulose acetate phthalates; epoxies; ethylene copolymers: ethylene-vinyl acetate-methacrylic acid, ethylene-acrylic acid copolymers; methylpentene polymers; modified phenylene oxides; polyamides; melamine formaldehydes; phenolformaldehydes; phenolic resins; poly(orthoesters); poly(cyanoacrylates); polydioxanone; polycarbonates; polyesters; polystyrene; polystyrene copolymers: poly(styrene-co maleic anhydride); urea-formaldehyde; urethanes; vinyl resins: vinyl chloride-vinyl acetate copolymers, polyvinyl chloride and mixtures of two or more of these.

Polymers that are biodegradable are also useful in the present invention. As used herein, a polymer is biodegradable if is not water soluble, but is degraded over a period of several weeks when placed in an application environment. Examples of biodegradable polymers that are useful in the present invention include biodegradable polyesters; starch-polyester alloys; styrene-maleic anhydride copolymers; poly(methylvinyl ether-maleic acid); starch; starch-PCL blends; polylactic acid (PLA)-starch blends; polylactic acid; poly(lactic acid-glycolic acid) copolymers; PCL; cellulose esters; cellulose acetate butyrate; starch esters; starch ester-aliphatic polyester blends; modified corn starch; polycaprolactone; poly(n-amylmethacrylate); ethyl cellulose; wood rosin; polyanhydrides; polyvinylalcohol (PVOH); polyhydroxybutyrate-valerate (PHBV); biodegradable aliphatic polyesters; and polyhydroxybutyrate (PHB). A biodegradable aliphatic polyester such as BIONOLLE, from Showa High Polymer, Tokyo, Japan, is preferred.

When the active ingredient is a pesticide, herbicide or plant growth regulator, a preferred matrix polymer is selected from the group consisting of poly (methylmethacrylate) and poly(styrene-co maleic anhydride). Poly(methylmethacrylate) is a particularly preferred matrix polymer, and it is preferred that the poly (methylmethacrylate) has a weight average molecular weight of from about 100,000 to about 400,000, even more preferred that the poly(methylmethacrylate) has a weight average molecular weight of from about 120,000.

Matrix Polymer Plasticizer

Another component of the subject formulation is a "matrix polymer plasticizer", which may also be referred to herein as simply a "plasticizer". The plasticizer of the present formulation can be any material that has a plasticizing effect upon the matrix polymer at about 25° C. when intermixed with the matrix polymer, i.e., the plasticizer is capable of improving the ductility of the matrix polymer. The plasticizer is especially a material that is capable of plasticizing poly(methyl methacrylate) (PMMA) or poly (sytrene co-maleic anhydride) (PSMA). There may be one or more plasticizers present in the formulation. For the weight ratio of such plasticizer to matrix polymer, the range up to 1:1.5 wt/wt (particularly from about 1:200 to about 1:1.5 wt/wt) includes most of the likely uses, and for making effectively rigid but not brittle formulations, the range 1:100–1:4.5 wt/wt is generally suitable.

Thus, according to the present invention, the plasticizer may be at least one material that is selected from the group consisting of high-boiling esters of polybasic acids; phosphoric acid derivatives; phosphorous acid derivatives; phosphonic acid derivatives; substituted fatty acids; high-boiling glycols; polyglycols; polyoxyalkylenes and glycerol each optionally substituted and optionally terminally esterified; pentaerythritols and derivatives; sulphonic acid derivatives; epoxy derivatives; chlorinated paraffins; block copolyesters; block polyester copolyethers; polymeric esters; WOLFLEX-BUT; and mixtures thereof.

Examples of suitable plasticizers are:

(A) High boiling esters of polybasic acids, such as:
(i) phthalates and isophthalates, particularly compounds of the formula:

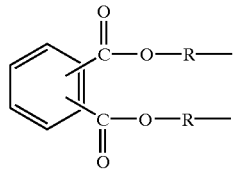

where $R_1$ is $C_{1-20}$ alkyl, cycloalkyl or benzyl, preferably $C_{5-11}$ alkyl, cyclohexyl or benzyl, especially isoheptyl, isoocytl, isononyl, isodecyl and isoundecyl. For example di-isodecylphthalate (JAYFLEX DIDP), di-isooctylphthalate
(JAYFLEX DIOP), di-isoheptylphthalate (JAYFLEX 77 DHIP), di-baptylphthalate,
di-rindecylphthalate, di-isononylphthalate (JAYFLEX DNIP), di-isoundecylphthalate
(JAYFLEX DIUP), diisodecylphthalate (REOMOL DiDP), di-isobutylphthalate
(REOMOL DiBP), di-tridecylphthalate, butyl benzyl phthalate (KETJENFLEX 160);

(ii) citrates; International Patent Application No. PCT/GB 93/01689 discloses a range of doubly esterified hydroxycarboxylic acids having at least 3 ester groups in its molecule. A particularly preferred example from that disclosure is acetyl tri-n-butyl citrate (ESTAFLEX). Further citrates of the formula:

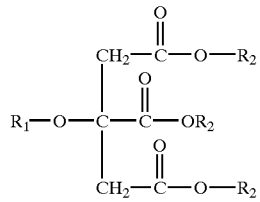

where $R_1$ is hydrogen or $C_{1-10}$ alkyl, and $R_2$ is $C_{1-10}$ alkyl, $C_{1-10}$ alkoxy or $C_{1-10}$ alkoxyalkyl. When $R_1$ and $R_2$ are alkyl each is preferably selected from straight or branched chain, methyl, ethyl, propyl, butyl, pentyl, hexyl, iso-propyl, isobutyl, or ethoxyethyl, propoxyethyl, butoxyethyl, butoxy isopropyl and butoxyethoxyethyl are encompassed by the present invention. Particular examples are: triethyleitrate, trimethylcitrate, n-butyl tri-n-hexylcitrate (CITROFLEX B6), tri-n-butylcitrate (CITROFLEX 4).

(iii) fumarates;

(iv) glutarates such as diester ether alkyl (PLASTHALL 7050);

(v) adipates, such as those of the formula $R_1$—O—C(O)—$(CH_2)_4$—C(O)—$OR_2$
where $R_1$ and $R_2$ which may be the same or different are $C_{2-12}$ alkyl (e.g., butyl), $C_{2-12}$ alkoxyalkyl (e.g., butoxyethyl), for example, di-2-ethylhexyl adipate (REOMOL DOA), di-isodecyl adipate, di-isononyl adipate, dioctyl adipate; other esterified radicals may be for example $C_1$–$C_{12}$ alkyl, aryl, or aralkyl.

(vi) sebacates of the formula $R_1$—O—C(O)—$(CH_2)S$—C(O)—O—$R_1$ where $R_1$ is $C_{2-15}$ alkyl or $C_{2-15}$ alkoxyalkyl, for example, di-octyl sebacate, di-dodecyl sebacate, di-butoxyethyl sebacate, or di-n-butyl sebacate;

(ix) azelates of the formula $R_1$—O—C(O)—$(CH_2)_7$—C(O)—$R_1$ where $R_1$ is $C_{2-12}$ alkyl, benzyl, or $C_{2-12}$ alkoxyalkyl, for example, di-n-butyl azelate and di i-octyl azelate;

(B) high-boiling glycols, polyglycols, polyoxyalkylenes and glycerol each optionally
substituted and optionally terminally esterified:
(i) high molecular weight glycols such as triethylene glycol diacetate (ESTOL 1593),
triethylene glycol caprylate (PLASTHALL 4141), alkyl ethers/esters of general
formula $R_2$—(O—$CH_2$—$CH_2$)$_n$—O—$R_1$ where $R_1$ is alkyl or —C(O)—alkyl, $R_2$ is alkyl and
n is 2 to 100, for example MORTON TP90B where $R_2$ IS $C_4H_9$— and n is 2, REOMOL
BCD or BCF where $R_1$ is —C(O)-alkyl, $R_2$ is $C_4H_9$— and n is 2, MORTON TP759
where $R_2$ is $C_4H_9$—, n is 2 and $R_1$ is [—C(O)]$_2$-alkyl in the form of a residue of adipic acid, compounds of such formula where $R_1$ is —C(O)—$C_nH_{2n+1}$, particularly
up to n=20, e.g. lauryl when n is 12, palmitate when n is 15 or oleate when n is 15 and unsaturated, stearyl when n is 17, $R_2$ is sorbitan and n is up to 20, for example TWEEN 80 in which $R_2$ is sorbitan monooleate, $R_1$ is lauryl arid n is 20;

and such compounds containing irregularly spaced ether linkages, for example the compounds of the formula above in which $R_1$ is hydrogen, $R_2$ is alkylphenyl where the alkyl is $C_{2-12}$ alkyl, and n is 2 to 100, for example, IGEPAL CA210 where the alkyl is $C_8$ alkyl and n is 2, IGEPAL CA510 which is the same as CA210 except that n is 5, TRITON X-100 and TRITON X-405 which is the same as IGEPAL CA510 except that n is 10 and 40 respectively, PLASTHALL CPH27N, CPH30N and CPH39 where $R_1$ is hydrogen, $R_2$ is $CH_3$—$(CH_2)_{10}$—C(O)— and n is 10, 5 and 15 respectively, PLASTHALL CPH39N and CPH4 IN in which $R_1$ is hydrogen, $R_2$ is $CH_3$—$(CH_2)_7$—CH=CH—$(CH_2)_7$—C(O)— and n is 5 and 15 respectively; PEG 2000, PEG 6000 and PEG 10000 where $R_1$ and $R_2$ are both hydrogen and n is 50, 150 and 200 respectively;

(ii) examples of polyglycols are poly(propylene glycol) (PPG 100, PPG 725, PPG 425), poly(ethylene) glycol (PEG 300, PEG 200);

(iii) examples of glycerol derivatives are glycerol tricaprolate, glycerol tributyrate;

(iv) pentaerythritols and derivatives;

(C) sulphonic acid derivatives such as toluenesulphonamide (KETJENFLEX 15, KETJENFLEX 8, KETJENFLEX 7, KETJENFLEX 3);

(D) epoxy derivatives such as the compounds of formula $CH_3$—$(CH_2)_n$-A-$(CH_2)_n$—R in which the A is an alkene containing one or more double bonds (i.e. unsaturated fatty acids), n is up to 25 and R is $C_{2-15}$ alkyl, or epoxy derivatives of triglycerides containing one or more double bonds per fatty acid chain with chain lengths from $C_{6-26}$, such as epoxidized soya bean oil, epoxidised linseed oils, epoxidised octyl tallate, epoxidised glycololeate, e.g. LANKRO EDG, LANKRO GE, PARAPLEX G60, PARAPLEX G62, PLASTHALL E50, RHEOPLAS 39 and LANKRO L;

(E) substituted fatty acids such as palmitates, stearates, oleates, ricinoleates and laurates, for example, sorbitan monolaurate, sorbitan monooleate, poly(oxyethylene), sorbitan monolaurate (TWEEN 20), poly(oxyethylene)(4) lauryl ether (BRIJ 30), butyl acetyl ricinoleate (BAR);

(F) phosphoric acid derivatives (phosphates), particularly compounds of the formula O=P(OR)$_3$ where R is straight chain or branched $C_{1-25}$ alkyl, alkoxyalkyl (e.g. ethylene oxide chains, propylene oxide chains with 2 to 30 repeat units), phenyl, or phenylalkyl where the alkyl is straight chain or branched $C_{1-25}$, for example, isopropyl-phenyl. Particular examples are: phosphate ester (REOMOL 249), tri isopropyl phenyl phosphate (REOFOS 95); and phosphonic acid derivatives and phosphites;

(G) chlorinated paraffins such as CERECLOR 56L, CERECHLOR 552;

(H) polymeric esters such as those of the formula —O—C(O)—$R_1$—C(O)—O—$R_2$—O— in which $R_1$ and $R_2$ are both independently $C_{2-12}$ alkylene, $R_2$ may be derived from a diol such as 1,2-propanediol, 1,3 butanediol, 1,4-butanediol or 1,6-hexanediol; for example;

(i) polyester glutarates having molecular weights from 2000 to 20,000, e.g. PLASTHALL 550, PLASTHALL 7046, PLASTHALL 7092, PARAPLEX P550, PARAPLEX P7035;

(ii) polyester adipates having a molecular weight from 200 to 20000, for example, PLASTHALL 643, PLASTHALL 650, poly(propylene) adipate for example LANKROFLEX PLA, LANKROFLEX PPL, LANKROFLEX PPA/3, PARAPLEX G56, PARAPLEX G59, DIOLPATE 214, and DIOLPATE 917, poly(1,3-butylene glycol-co-1,2-propylene glycol adipic acid) terminated with 2-ethylhexanol (SANTICIZER S409A; Mw=3700, available from Solutia Inc.), poly(neopentyl glycol-co-1,4-butylene glycol adipic acid) terminated with 2-ethylhexanol (SANTICIZER S433; Mw=3500, available from Solutia Inc.), poly(1,3-butylene glycol adipic acid) unterminated (SANTICIZER S430; Mw=2500, available from Solutia Inc.), poly(1,3-butylene glycol adipic acid) unterminated (SANTICIZER S421; Mw=1250, available from Solutia Inc.), poly(1,2-propylene glycol 5 adipic acid-co-phthalic acid) terminated with 2-ethylhexanol (SANTICIZER S438; Mw=1900, available from Solutia Inc.), poly(neopentyl glycol adipic acid) terminated with 2ethylhexanol (SANTICIZER S435; Mw=2500; available from Solutia Inc.), poly(1,2-propylene glycol adipic acid-co-phthalic acid) terminated with 2-ethylhexanol (SANTICIZER 431; Mw=1200; available from Solutia Inc.), poly(1,2-propylene glycol-co-1,4-butylene glycol adipic acid) terminated with 2 ethylhexanol (SANTICIZER S4212; Mw=950; available from Solutia Inc.), poly (1,3-butylene glycol adipic acid) terminated with mixed fatty acids (SANTICIZER S405; Mw=2000; available from Solutia Inc.), poly(1,2 propylene glycol adipic acid) terminated with 2-ethylhexanol (SANTICIZER S436; Mw=3500; available from Solutia Inc.), poly(1,2-propylene glycol-co-1,4-butylene glycol adipic acid) terminated with 2-ethylhexanol (SANTICIZER S449; Mw=3700; available from Solutia Inc.), poly(1,4-butylene glycol adipic acid), or poly(1,4-butylene glycol-co ethylene glycol adipic acid).

(iii) succinic polyesters;

(iv) sebacic polyesters having a molecular weight from 4000 to 10000, preferably 8000, for example, PLASTHALL 1070, (iv) DIOLPATE OL1696, DIOREX 570;

(v) lactone copolymers of the formula [—(O—C(O)—$R_1$—C(O)—O—$R_2$—O)]$_m$[—C(O)—$R_3$—O—]$_n$, where $R_1$ and $R_2$ are both independently $C_{2-12}$ alkylene, or $R_2$ may be derived from a diol such as 1,2-propanediol, 1,3-butanediol, 1,4-butanediol or 1,6-hexanediol, and $R_3$ is —$(CH_2)_5$-(based on caprolactone);

(vi) polyesters such as REOPLEX 346, REOPLEX 1102, REOMOL MD (ester of mixed adipic, glutaric and succinic acids with isodecanol), polycaprolactone triol (PCL TRIOL (300));

(I) WOLFLEX-BUT;

Preferred plasticizers are the polymeric esters, high-boiling glycols, polyglycols, polyoxyalkylenes and glycerol each optionally substituted and optionally terminally esterified, epoxidised soyabean oils, adipates, sebacates, phosphate esters, phthalic anhydride, phthalates, citrates, castor oil, chlorinated paraffins and toluene sulphonamide derivatives.

When poly(methyl methacrylate) or poly(styrene-co-maleic anhydride) is the matrix polymer, a particularly preferred matrix polymer plasticizer is one selected from the group consisting of phthalic anhydride, poly(vinyl acetate) and dibutyl phthalate. When PMMA is the matrix polymer, the preferred matrix polymer plasticizer is poly(vinyl acetate) or dibutyl phthalate.

Composition of the Formulations

In combination with the selection of suitable components for producing the subject formulations, as described above, it is also important that the formulations contain the correct relative amounts of active ingredient, matrix polymer and matrix polymer plasticizer, in order to obtain the advantageous properties of the formulations.

It is usually desirable that the amount of active ingredient be as high as possible while retaining the other advantageous properties of the formulation. The preferred range for the level of the active ingredient in a subject formulation is from 1% to 60%, more preferably 5% to 50%, even more preferably 20% to 45%, and yet more preferably over about 40% (expressed as percent of the weight of the solids in the formulation). If the remainder of the formulation consists of the matrix polymer and the matrix polymer plasticizer, the relative amounts of each of these depend upon the chemicals being used and the rate of release of active ingredient that is desired. By way of example, if the active loading is 40% by weight, then the remaining 60% of the formulation can consist essentially of the matrix polymer and the plasticizer, or additional materials can be added, as will be discussed below. The ratio of matrix polymer-to-plasticizer has been described briefly above, but will now be described in more detail.

It is preferred that the formulation contains a sufficient amount of the plasticizer to provide a release rate for the active ingredient that matches a selected release rate. The "selected release rate" is the rate at which active ingredient is released from a formulation in order to provide an effective level of active ingredient in the application environment immediately surrounding the formulation at a time or during a period that is selected by the user. The "application environment immediately surrounding the formulation" is meant to include the region within about 1 mm of the formulation, preferably about 5 mm, more preferably about 10 mm, and yet more preferably within about 25 mm of the formulation. An "effective level" of the active ingredient is a concentration at which the active ingredient is effective to protect against the target pest.

It is also preferred that the level of the active ingredient does not exceed a toxic level during the period in which the active is being released by the formulation. A "toxic level", or "toxic limit", of the active ingredient, as those terms are used herein, means a concentration of the active ingredient that is harmful to an entity other than the target pest, where the entity is one that the user desires to spare from harm. For example, a toxic level includes a concentration at which the active is phytotoxic to a seed or a plant; a concentration that is harmful to wildlife which may contact the active; and a concentration that is harmful to persons who make, transfer, handle, store, load and/or apply the active.

Figure 1:
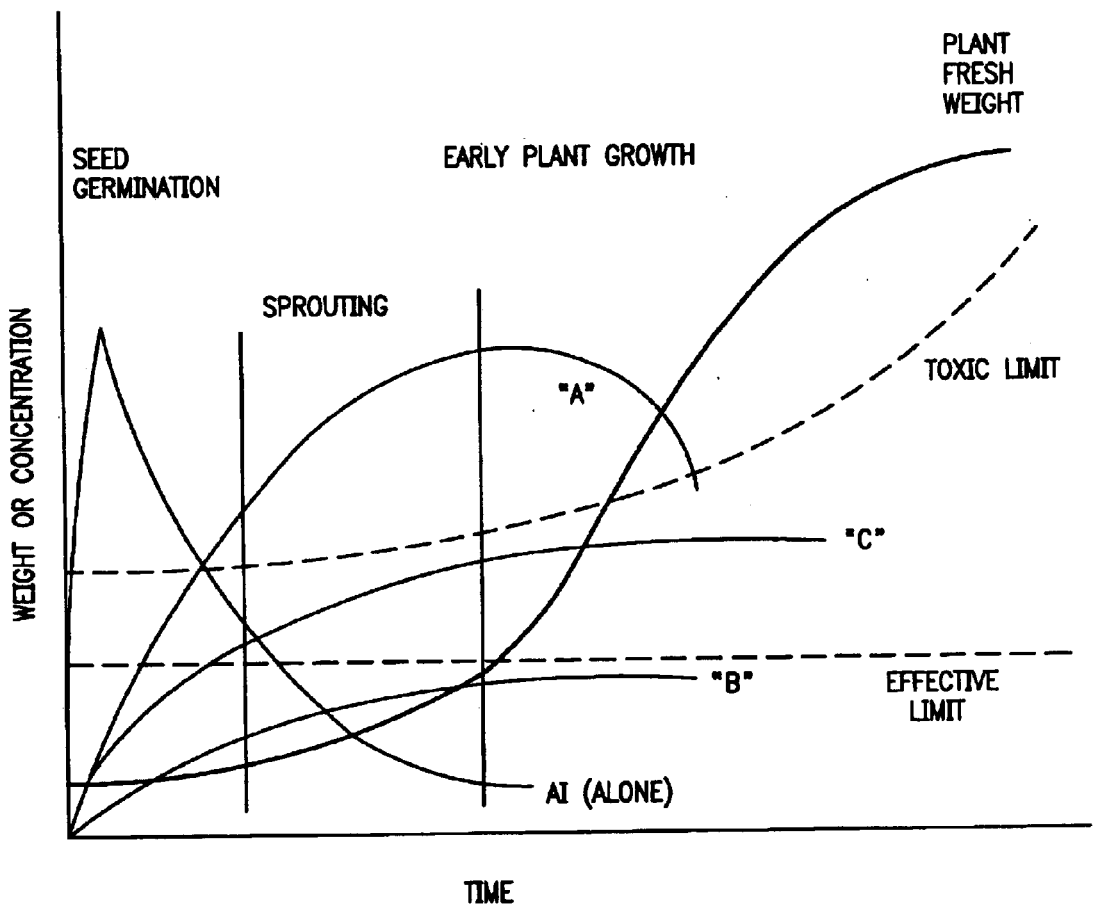

The concept of a formulation that contains a sufficient amount of the plasticizer, and a certain compatibility between the matrix polymer and the plasticizer, to provide a release rate for the active ingredient that matches a selected release rate may be more easily envisioned by referring to FIG. 1. (Since FIG. 1 is intended to be illustrative only, no particular significance is to be placed on the precise location or relationship of the parameters depicted, other than for the illustrative example described below). Plant fresh weight is shown as increasing with time from planting, through germination, sprouting and early plant growth stages. Effective and toxic limits of a pesticide or herbicide are illustrated by dashed lines. If the toxic limit represents the phytotoxic level of the active, it not uncommon for the level to change as the plant passes through different growth stages. The objective of a controlled release formulation of the present invention is to provide a release rate for the active that insures a level of the active in the environment surrounding the seed and/or plant that is above the effective limit and below the toxic limit. It is particularly useful if the active is present at this effective level during the germination, sprouting and early growth stages of the plant, when plant defensive mechanisms may not have matured. When it is said that the release rate of the active from the subject formulation "matches" a selected release rate, it is meant that the release rate of the active is controlled to provide an effective level of active during critical periods of plant development.

In a formulation containing an active ingredient with a matrix polymer and a plasticizer, the level of the active ingredient can range from about 1% to about 60% by weight of the dry ingredients of the formulation, but is preferably at least about 5% by weight, more preferably at least about 10%, even more preferably at least about 20%, and yet more preferably at least about 30%, or more.

Depending upon the release rate that is selected and the compatibility of the active, the matrix polymer and the plasticizer, the amount of these three components is varied to match the selected release rate. In general, the level of the active is set as high as possible without exceeding a toxic limit. A matrix polymer is then selected. The matrix polymer is one that is sufficiently compatible with the active ingredient that a mixture of the matrix polymer, the active, and a plasticizer can be formed into a solid microparticle having a uniform physical structure, but that will release the active over a period of no more than several months when placed out of doors on a growing plant or in the soil. When it is said that a microparticle has a "uniform physical structure" it is meant that the active ingredient is distributed essentially uniformly throughout the microparticle and is not concentrated on the surface of the microparticle. A suitable plasticizer according is then selected according to the criteria described above and the ratio of matrix polymer-to-plasticizer is set to match the selected release rate.

By way of example, when tebuconazole is the active ingredient, and with poly(methyl methacrylate) as the matrix polymer and dibutly phthtlate as the plasticizer, the tebuconazole is present at levels of about 20% to 60% by weight of the dry formulation, preferably 30% to 50%, more preferably about 40%; the remainder of the formulation comprises PMMA and DBP, and the weight ratio of PMMA to DBP is from about 99:1 to about 90:10, preferably from about 98:2 to 96:4. If phthalic anhydride (PA) or poly(vinyl acetate) (PVA) is substituted for dibutyl phthalate as the plasticizer, the PMMA:PA or PMMA:PVA ratio is from about 95:5 to 50:50, preferably from about 90:10 to 60:40, more preferably from about 90:20 to 70:30, in order to obtain substantially the same release rate.

As mentioned above, it is preferred that most or all of the active ingredient be enclosed within the microparticles, rather than to be present in the formulation as separate crystals or on the surface of the microparticles. Formulations having a high percentage of the active ingredient in separate crystals or on the surface of the microparticles are prone to having the active readily dissolved or leached away from the formulation with no benefit of a controlled release function. The relative amount of the active that is released into the environment without control is termed the "readily extractable active" (REA). As used herein, REA means the percent by weight of the total active ingredient that was added to the formulation that dissolved in water in a test such as the following:

REA was measured by adding the formulation to be tested to water in each of two test tubes at room temperature, about 25° C. The total amount of the formulation added to one test tube was sufficient to provide an amount of the active ingredient that was about 80% of its solubility limit in water at that temperature. The total amount of the formulation added to the other test tube was sufficient to provide an amount of the active that was about 120% of the solubility limit. Both tubes were then shaken vigorously for about 200 shakes. A sample of the mixture was removed from each tube and filtered through a 0.45 micron PTFE filter. The concentration of the active in the filtered liquid was measured in each of the two test tubes and the percentage of the total amount of active that had been released into the water was calculated. The value of the total amount of active that was released into the water was divided by the total amount of active that was initially added to the tube and the average of those values was multiplied by 100 and reported as percent REA for the formulation.

It is preferred that the formulations of the present invention have an REA value of less than 25% of the total active ingredient in the formulation, more preferably less than 15% of the total active ingredient in the formulation, even more preferably less than 10% of the total active ingredient in the formulation, and yet more preferably less than 5% of the total active ingredient in the formulation.

When the formulation includes tebuconazole with PMMA or PSMA as the matrix polymer, and either PA, PVA, or DBP as the plasticizer, the amount of readily extractable active ingredient (REA) in an excess of water at 25° C. is less than about 25% of the total active ingredient in the formulation, preferably less than about 15%, and more preferably less than about 10%.

Other Components

It is intended that one or more components, in addition to the active, the matrix polymer and the plasticizer, can be a part of the subject formulations and that the resulting formulations will still be within the scope of the invention. Such other components can be, for example, surfactants; hydrogels; inorganic carriers, such as: silicates: glass powder; synthetic precipitated amorphous silica—HYSIL 257, HYSIL HOA, or SIPERNAT 50S; synthetic precipitated amorphous calcium silicate—HUBERSORB 600; synthetic precipitated aluminosilicate—ZEOLEX; or naturally occurring amorphous silica—FILTERCEL; carbonates, such as: powdered calcium carbonate; talc; phosphates; sulfates; organic carriers, such as: starches: cornstarch, oat starch, cellulose, proteins and protein meals; fillers; crosslinkers; dyes; wetting agents; defoamers; and the like. It should be understood, however, that any such other component that is a part of the subject formulation is one that does not substantially disrupt or modify the chemical and/or physical compatibility relationship between the matrix polymer and the active ingredient that is discussed above. For example, another ingredient or component of the formulation would "substantially disrupt or modify" the chemical compatibility between the matrix polymer and the active if it altered the REA of a subject formulation by more than 20%, or if altered the release rate profile of a subject formulation so as to render it less effective against the targeted pest than the formulation without the other ingredient(s).

Methods of Making the Formulation

The method of making the subject formulation is not critical and any method can be used so long as it results in a product having the advantageous properties of the subject formulation. It is preferred, however, that the subject formulation be made by intermixing the matrix polymer and the active ingredient with a sufficient amount of the matrix polymer plasticizer to form a mixture, and then forming the mixture into microparticles or microcapsules having a release rate for the active ingredient that matches a selected release rate when the formulation is in the application environment. Suitable methods for mixing ingredients and forming microparticles and microcapsules are known in the art, and several of these methods are described by Theis, C., in the chapter on *Microencapsulation*, at pp. 628–651, in Vol. 16 of *Kirk-Othmer Encyclopedia of Chemical Technology*, Fourth Ed., John Wiley & Sons, New York (1995); and by Sliwka, W., in *Angew. Chem. internat. Edit.*, 14(8):539–550 (1975).

The components of the formulation can be intermixed by melting the matrix polymer, the active ingredient and the plasticizer and intermixing the molten components. The molten mixture can then be cooled to form a solid. It is preferred that the solid be formed into particles having a size within a desired size range, as will be described in detail below.

Alternatively, the components can be placed into solution in a solvent, preferably and organic solvent, and intermixed while they are in solution. The subject formulation can then be obtained by removing, neutralizing, or otherwise negating the solvating effect of the solvent. Commonly, solvent removal is done by evaporating the solvent from the solution and thereby leaving the subject formulation in solid form. As mentioned above, it is preferred that the solid be in particulate form with the particles being within a desired size range.

When it is said that the components are placed in solution, it is meant to include not only true molecular-level solutions, but also mixtures where at least some part of, but not all, of each components is in a true solution, and the remainder is present as part of an emulsion, dispersion, micro-emulsion, suspension, colloidal suspension, or other solid-liquid mixture in which the solid is present as particles of less than 100 microns in size. However, it is preferred that each of the components be in a true solution in the solvent.

A preferred method for making the subject formulation by an emulsion method consists of preparing a solution of the active ingredient in an organic solvent along with the matrix polymer and the matrix polymer plasticizer. Generally, sufficient organic solvent is used to permit all, or most, of the matrix polymer, the active and the plasticizer to go into solution. It is preferred that the active ingredient be added to the organic solution in an amount that provides, in percent by weight, from about 0.1% to about 60% of the solution, more preferably from about 0.5% to about 25%, even more preferably from about 1% to about 10%, and yet more preferably from about 1.5% to about 8%. The matrix polymer is added to the organic solvent in an amount so as to consist of, in percent by weight of the organic solution, from about 0.3% to about 70%, more preferably from about 1% to about 40%, even more preferably from about 3% to about 25%, and yet more preferably about 3.5% to about 20%. The matrix polymer plasticizer is added to the organic solution in an amount so as to consist of, in percent by weight of the solution, from about 0.001% to about 30%, preferably from about 0.01% to about 20%, even more preferably from about 0.05% to about 10%, even more preferably from about 0.1% to about 8%, and yet more preferably from about 0.2% to about 6%.

By way of example, when the active ingredient is tebuconazole, the matrix polymer can be poly(methyl methacrylate) and the plasticizer can be dibutlyphthalate. A solution of these ingredients can be prepared in, for example, by adding 5–7 g tebuconazole, 6–8 g poly(methyl methacrylate) and 0.1–1 g dibutlyphthalate, to about 84 g to about 89 g of methylene chloride. This mixture is then mixed at room temperature by any conventional method of agitation until the ingredients and thoroughly intermixed and, preferably, dissolved.

A separate aqueous solution is then prepared that contains about 90 g of water. It is preferred, but not required, that the aqueous solution also contain a surfactant. When METHO- CEL A15LV is used as the surfactant, about 1 g of that material is dissolved in the 90 g of water by standard laboratory techniques. The aqueous solution is then preferably cooled, and a temperature of about 4° C. is more preferred.

The organic and aqueous solutions are intermixed while subjecting the mixture to high shear. For example, one solution can be added to the other over a period of about 15 sec. to about 1 minute, while the mixture is being agitated by a high shear mixer. A Silverson Model L4R high shear mixer with a 6-hole screen is suitable for small batches of the material. The mixture is agitated with the high shear mixer for about 3 minutes at the rate of 3 to form a milky emulsion. The emulsion can then be stirred with a low shear mechanical stirrer at room temperature under conditions that will cause the organic solvent to evaporate from the mixture. Agitation for about 20 hours at room temperature, for example, is sufficient for the removal of methylene chloride.

This procedure yields an aqueous emulsion of microparticles having an average size of about 4–8 microns; having an active loading of about 40% by weight of the tebuconazole in the microparticles; having an REA of under about 5%; and having no visible crystals of tebuconazole. The aqueous emulsion can be used as is, or the microparticles can be separated from the liquid by centrifugation or filtration and dried to form a powder.

When the subject formulation is formed into microparticles or microcapsules, it is preferred that the particles be of an average size that is small enough that they can easily be handled in conventional spray equipment without clogging, and that adhere tightly to seeds when used in a seed treatment. When the term "microparticles" is used alone to describe the physical form of the subject formulation, it is intended to include microcapsules.

Preferred microparticles of the subject formulation have an average size of about 100 microns or less. As used herein, "average size" means the average nominal diameter of the microparticles. It is more preferred that the microparticles have an average size of 50 microns or less; 20 microns or less is even more preferred; and 10 microns or less is yet more preferred. Expressed another way, it is preferred that at least 80% of the microparticles have a size of 100 microns or less; 80% having a size of 20 microns or less is more preferred; and 80% having a size of 10 microns or less is yet more preferred.

Methods of Using the Formulations

The controlled release formulations of the present invention can be used wherever controlled release formulations are conventionally used. In particular, they are useful in a method for providing controlled release of pesticides, herbicides and plant growth regulating compounds into an application environment to protect seeds and plants from animal and plant pests, or to regulate growth.

When the active ingredient is a pesticide or herbicide, the present method can be used to protect the seed, roots and/or the above- and below-ground parts of field, forage, plantation, glasshouse, orchard or vineyard crops, ornamentals, plantation or forest trees. The seeds and plants on which the present invention is useful can be of any species. However, they are preferably plant species that are agronomically important. Of particular importance are corn, peanut, canola/rapeseed, soybean, curcubits, crucifers, cotton, rice, sorghum, sugar beet, wheat, barley, rye, sunflower, tomato, sugarcane, tobacco, oats, as well as other vegetable and leaf crops. The subject formulation is particularly useful on the seeds or plants of corn, soybeans, wheat, or cotton.

In one embodiment of the invention, the seed or plant is transgenic. The transgenic seed or plant on which the present invention is useful is engineered to express a desirable characteristic and, in particular, to have at least one heterologous gene encoding for the expression of a protein that is pesticidally active and, in particular, has insecticidal activity. The heterologous gene in the transgenic seeds and plants of the present invention can be derived from a microorganism such as *Bacillus, Rhizobium, Pseudomonas, Serratia, Trichoderma, Clavibacter, Glomus, Gliocladium* and mycorrhizal fungi. In particular, it is believed that the present method would be especially beneficial when the heterologous gene is one that is derived from a *Bacillus* sp. microorganism and the protein is active against corn root worm. It is also believed that the present method would be especially beneficial when the heterologous gene is one that is derived from a *Bacillus* sp. microorganism and the protein is active against European corn borer. A preferred *Bacillus* sp. microorganism is *Bacillus thuringiensis.*

In one embodiment of the method of the present invention, the controlled release formulation is applied to a seed. Although it is believed that the present formulation can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment with the formulation. Within the limitations just described, it is believed that the treatment can be applied to the seed at any time between harvest of the seed and sowing of the seed; during or after sowing; and/or after sprouting.

When it is said that a seed is "treated" with the controlled release formulation, such treatment is meant to include those practices in which the formulation is applied to the soil, rather than, or in addition to, the seed. For example, such treatments as the application of the formulation in bands, "T"-bands, or in-furrow, at the same time as the seed is sowed are considered to be included in the present invention.

The subject formulation can be applied "neat", that is, without any diluting or additional components present. However, the formulation is typically applied to the seeds in the form of a coating that may contain one or more other desirable components including but not limited to liquid diluents, binders, fillers for protecting the seeds during stress conditions, and other ingredients to improve flexibility, adhesion and/or spreadability of the coating. In some situations, it may be desirable to add drying agents such as calcium carbonate, kaolin or bentonite clay, perlite, diatomaceous earth or any other adsorbent material. Use of such components in seed treatments is known in the art. See, e.g., U.S. Pat. No. 5,876,739. The skilled artisan can readily select desirable components to use in the seed coating, depending on the seed type to be treated and the particular controlled release formulation that is selected.

The controlled release formulation of the present invention can be made into and/or applied to seeds or plants in the form of a suspension; emulsion; slurry of particles in an aqueous medium (e.g., water); wettable powder; wettable granules (dry flowable); and dry granules.

Other conventional inactive or inert ingredients can be incorporated into the coating, or other application formulation. Such inert ingredients include but are not limited to: conventional sticking agents, dispersing agents such as methylcellulose (METHOCEL A15LV or METHOCEL A15C, for example, serve as combined dispersant/sticking agents for use in seed treatments), polyvinyl alcohol (e.g., ELVANOL 51-05), lecithin (e.g., YELKINOL P), polymeric dispersants (e.g., polyvinylpyrrolidone/vinyl acetate PVP/VA S-630), thickeners (e.g., clay thickeners such as VAN GEL B to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's, vol. 1, *"Emulsifiers and Detergents,"* MC Publishing Company, Glen Rock, N.J., U.S.A. (1996). Additional inert ingredients useful in the present invention can be found in McCutcheon's, vol. 2, *"Functional Materials,"* MC Publishing Company, Glen Rock, N.J., U.S.A. (1996).

The controlled release formulations of the present invention can be applied to seeds by any standard seed treatment methodology, including but not limited to mixing in a container (e.g., a bottle or bag), mechanical application, tumbling, spraying, and immersion. Any conventional active or inert material can be used for contacting seeds with pesticides according to the present invention, such as conventional film-coating materials including but not limited to water-based film coating materials such as SEPIRET (Seppic, Inc., Fairfield, N.J.) and OPACOAT (Berwind Pharm. Services, Westpoint, Pa.).

The formulation may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The treated seeds may also be enveloped with a film overcoating to protect the coating. Such overcoatings are known in the art and may be applied using conventional fluidized bed and drum film coating techniques.

If the controlled release formulation is applied to the seed as one ingredient of a coating, the seeds can be coated using a variety of methods including imbibition, solid matrix priming, coating, spraying and dusting. Seed treatments can take a variety of forms including, suspension concentrates, solutions, emulsions, powders and granules, as well as using polymeric carriers or stickers. For example, the coating process can comprise spraying a composition comprising the formulation onto the seed while agitating the seed in an appropriate piece of equipment such as a tumbler or a pan granulator.

In one embodiment, when coating seed on a large scale (for example a commercial scale), typically seed is introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the active ingredient in the controlled release formulation, the desired concentration on the finished seed, and the like. The treatment composition can be applied to the seed by a variety of means, for example by a spray nozzle or revolving disc. The amount of liquid is typically determined by the assay of the formulation and the required rate of active ingredient necessary for efficacy. As the seed falls into the treatment equipment the seed can be treated (for example by misting or spraying with the seed treatment composition) and passed through the treater under continual movement/tumbling where it can be coated evenly and dried before storage or use.

In another embodiment, a known weight of seeds can be introduced into the treatment equipment (such as a tumbler, a mixer, or a pan granulator). A known volume of seed treatment composition can be introduced into the treatment equipment at a rate that allows the seed treatment composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In still another embodiment, seeds can be coated in laboratory size commercial treatment equipment such as a tumbler, a mixer, or a pan granulator by introducing a known weight of seeds in the treater, adding the desired amount of seed treatment composition, tumbling or spinning the seed and placing it on a tray to thoroughly dry.

In another embodiment, seeds can also be coated by placing the known amount of seed into a narrow neck bottle or receptacle with a lid. While tumbling, the desired amount of seed treatment composition can be added to the receptacle. The seed is tumbled until it is coated with the seed treatment composition. After coating, the seed can optionally be dried, for example on a tray.

In another embodiment, a powdered form of the subject formulation can be mixed directly with seed. Optionally, a sticking agent, e.g., polyglycol, can be used to adhere the powder to the seed surface. For example, a quantity of seed can be mixed with a sticking agent and optionally agitated to encourage uniform coating of the seed with the sticking agent. The seed coated with the sticking agent can then be mixed with the powdered controlled release formulation. The mixture can be agitated, for example by tumbling, to encourage contact of the sticking agent with the powdered material, thereby causing the powdered material to stick to the seed.

The subject formulation can also be applied directly to plants by any method that is conventionally used for the application of, for example, pesticides to plants. Such methods can include spraying, dripping, wicking, dusting, or any other convention method. One advantage of the small microparticles of the present formulation is that their small size permits an even coverage of plant stems and leaves where the distance between particles of the formulation is small. Thus, the formulation is more effective in contacting pests that damage the plant.

When the active ingredient is a herbicide, the formulation can be applied to the soil in a field in any manner that is conventionally used for the application of a herbicide.

The present invention also provides a seed or a plant that has been treated by the method described above.

Another embodiment of the invention is a seed or a plant that is protected against one or more pests as a result of having been treated with the subject formulation Seeds that have been treated with the subject formulation can be used for the propagation of plants in the same manner as conventional treated seed. The treated seeds can be stored, handled, sowed and tilled in the same manner as a seed treated with, for example, a pesticide. Safety measures that are appropriate for the active ingredient of the formulation should be taken to limit contact of the treated seed with humans, food or feed materials, water and birds and wild or domestic animals.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1

This example illustrates the preparation of controlled release formulations having tebuconazole as the active ingredient with poly(methyl methacrylate) and phthalic anhydride as the matrix polymer and matrix polymer plasticizer, respectively.

Hydroxypropyl cellulose (1.08 g, METHOCEL A15LV, available from Dow Chemical Co.) was added to water (82.81 g) in a 400 ml beaker with mild stirring and the aqueous solution was cooled in an ice bath to about 4° C. In a separate beaker an organic solution was prepared that contained tebuconazole (6.44 g, of any commercial grade and supplier), phthalic anhydride (2.87 g, Aldrich Cat. No. 04905), and poly(methyl methacrylate) (6.8 g, 350,000 weight average molecular weight, available from Aldrich) in 93.50 g of methylene chloride. The organic solution was stirred at room temperature until all of the solid ingredients were in solutions.

The organic solution was then poured into the aqueous solution over a period of about 30 sec. while the mixture was being agitated with a high shear mixer (Silverson Model L4R equipped with a six-hole screen) set at a speed of 3. Mixing was continued for three minutes until the mixture formed a milky emulsion. The emulsion was then stirred with a standard mechanical stirrer for 20 hours at room temperature, or until the methylene chloride had evaporated from the solution. The white slurry that remained (approx. 100 g) contained microparticles having an average particle size of 6.36 microns. In a photomicrograph, the micropar- The emulsion provided the tebuconazole in a form that could be used directly for application to seeds, soil, or plants. Alternatively, the water could be removed from the slurry and the microparticles could be made into a dry powder, as described below.

A portion of the emulsion was filtered through a filter paper in a buchner funnel and the solids retained on the filter paper were washed with water until it was no longer sticky. The solids were dried by vacuum filtration and a white powder was obtained.

EXAMPLE 2

This illustrates the preparation of the controlled release formulation with tebuconazole at several loading levels and with the use several different matrix polymers and matrix polymer plasticizers.

Microparticles of the subject controlled release formulation were prepared by the same method as described in Example 1, except that PMMA having different molecular weights, and poly(styrene-co-maleic anhydride) (PSMA) were substituted for the matrix polymer and poly(vinyl acetate) was substituted for the plasticizer. Microparticles from these various formulations had the properties shown in Table 1.

TABLE 1

Composition of controlled release formulations with tebuconazole.

| SUSPENSION NO. | 1 | 2 | 3 | 4 | 5 | 6 | 7 |
|---|---|---|---|---|---|---|---|
| ACTIVE INGREDIENT LEVEL[a] | 40% | 40% | 40% | 40% | 40% | 40% | 40% |
| Tebuconazole[b] LOADING (gm) | 6.44 | 6.44 | — | 6.78 | 7.23 | 6.92 | 7.04 |
| PMMA 350,000 MW[c] (gm) | 6.8 | 6.8 | 5.16 | — | — | — | — |
| PMMA 120,000 MW[c] (gm) | — | — | — | 8.04 | 5.48 | — | — |
| PSMA[d] (gm) | — | — | — | — | — | 7.3 | 7.43 |
| Poly(vinyl acetate)[e] (gm) | — | — | — | 3.38 | — | 3.08 | — |
| Phthalic anhydride (gm) | 2.87 | 2.87 | 5.03 | — | 5.35 | — | 3.13 |
| Methocel Al5LV[f] (gm) | 1.08 | 1.08 | 1.13 | 1.27 | 1.20 | 1.14 | 1.17 |
| De-ionized water (gm) | 82.81 | 82.81 | 81.90 | 79.70 | 80.74 | 81.56 | 81.23 |
| Total | 100% | 100% | 100% | 100% | 100% | 100% | 100% |
| 100% AI basis | 70/30 | 70/30 | 50/50 | 70/30 | 50/50 | 50/30 | 50/30 |
| Properties | | | | | | | |
| % AI | 6.65 | 6.71 | 6.84 | 7.76 | 7.29 | 7.1 | 7.25 |
| Initial % REA[g] | 3.21–3.47 | 2.8 | 3.5 | 3 | 4.8 | 4.2 | 3.1 |
| Particle size (avg.; microns) | 6.36 | 5.89 | 4.73 | 5.2 | 4 | 57.39 | 4.7 |

Figure 2:
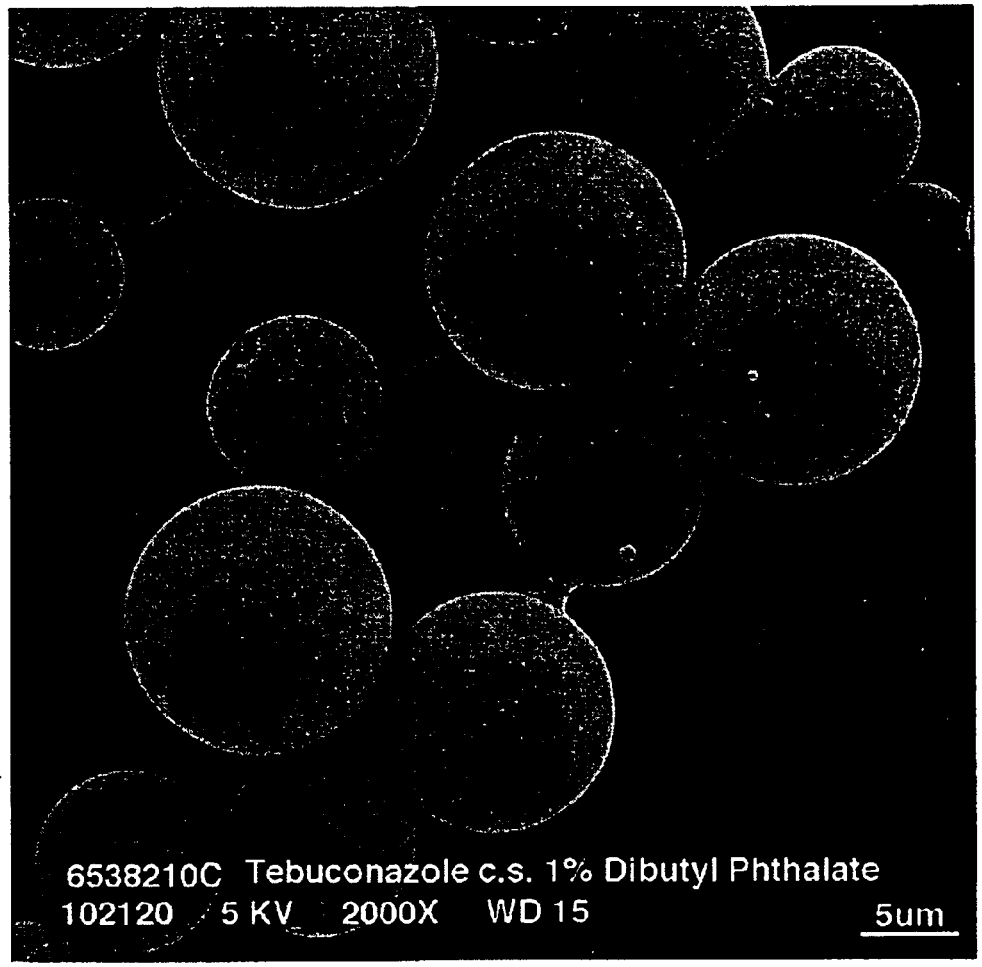

Notes: [a]The Active Ingredient Loading Level is defined as the weight % of active ingredient in the microparticles based on microparticle-only weight; e.g., without water.
[b]Tebuconazole is a fungicide preparation having a water solubility of 32 ppm and a normal melting point of 105° C.
[c]PMMA is poly(methyl methacrylate); 120,000 MW means a weight average molecular weight (MW) of 120,000; 350,000 MW means a weight average molecular weight of 350,000.
[d]PSMA is poly(styrene-co-maleic anhydride); 75:25 monomer ratio; 1,900 number average molecular weight.
[e]Poly(vinyl acetate) has a weight average molecular weight of 18,000.
[f]METHOCEL is hydroxypropylcellulose available from Dow Chemical Co.
[g]R.E.A. means Readily Extractable Active.

ticles appeared to be similar to those shown in FIG. 2, except the overall size range was smaller than for the particles shown in FIG. 2. The emulsion contained 6.65% by weight tebuconazole and had an initial REA of about 3.3%. The weight ratio of the matrix polymer-to-plasticizer was 70:30.

EXAMPLE 3

This example illustrates the preparation of microparticles containing tebuconazole at 40% loading with several combinations of matrix polymer and matrix polymer plasticizer.

Microparticles of the subject controlled release formulation were prepared by the same method as described in Example 1, except that a number of different combinations of matrix polymer (PMMA, PSMA, and poly(butyl methacrylate) (PBMA)), and matrix polymer plasticizer (poly(vinyl acetate) (PVA), phthalic anhydride (PA), dibutyl phthalate (DBP) were tested. Microparticles from these various formulations had the properties shown in Table 2.

TABLE 2

Properties of tebuconazole blend formulations at 40% by weight tebuconazole loading.

| TEST NO. | MATRIX POLYMER (MP) | PLASTICIZER (MPP) | MP:MPP WEIGHT RATIO | REA % | PARTICLE SIZE (microns) | % ACTIVE[a] | COMMENTS |
|---|---|---|---|---|---|---|---|
| 1 | PMMA 350 | PVA | 90:10 | — | — | — | Failed; crystals formed |
| 2 | PMMA 350 | PVA | 70:30 | — | — | — | Failed; soft cake |
| 3 | PMMA 350 | PA | 90:10 | — | — | — | Failed; bad capsules |
| 4 | PMMA 350 | PA | 90:10 | 2% | 11.27 | 6.82% | |
| 5 | PMMA 350 | PA | 70:30 | 3.3% | 6.36 | 6.65% | |
| 6 | PMMA 350 | PA | 50:50 | 3.5% | 4.73 | 6.84% | |
| 7 | PMMA 120 | PVA | 90:10 | 2.5% | 5.67 | 7.38% | |
| 8 | PMMA 120 | PVA | 90:10 | 2% | 8.48 | 6.87% | |
| 9 | PMMA 120 | PVA | 90:10 | 2.1% | 8.48 | 6.58% | |
| 10 | PMMA 120 | PVA | 80:20 | 3.4% | 5.47 | 6.66% | |
| 11 | PMMA 120 | PVA | 70:30 | 3% | 5.2 | 7.76% | |
| 12 | PMMA 120 | PA | 50:50 | 4.8% | 4 | 7.29% | |
| 13 | PSMA | PVA | 70:30 | 4.2% | 57.39 | 7.1% | |
| 14 | PSMA | PVA | 70:30 | 4.8% | 7.36 | 6.54% | |
| 15 | PSMA | PA | 70:30 | 3.1% | 4.7 | 7.25% | |
| 16 | PBMA | PVA | 70:30 | — | — | — | Failed; large lump |
| 17 | PBMA | PA | 70:30 | 16.7% | 4.9 | 5.47% | |
| 18 | PMMA 120 | Citroflex A-4 | 90:10 | 2.2% | 7.66 | 6.73% | |
| 19 | PMMA 120 | Lignin acetate | 90:10 | 2% | 8.13 | 6.71% | |
| 20 | PVA | none | — | 19.7% | 9.01 | 19.7% | |
| 21 | Lignin acetate | none | — | 4% | 6.35 | 6.86% | |
| 22 | PMMA 120 | DBP | 90:10 | 3.1% | 7.46 | 6.47% | |
| 23 | PMMA 120 | DBP | 99:1 | 1.9% | 8.12 | 7.14% | |
| 24 | PMMA 120 | DBP | 98:2 | 1.9% | 8.54 | 6.59% | |
| 25 | PMMA 120 | DBP | 97:3 | 1.7% | 8.54 | 6.93% | |
| 26 | PMMA 120 | DBP | 95:5 | 2% | 8.55 | 8.29% | |
| 27 | PMMA 120 | DBP | 93:7 | 2.2% | 8.22 | 6.76% | |
| 28 | Polycarbonate A Diphenol | none | — | 0.65% | 8.76 | 6.59% | |
| 29 | PSMA | none | — | 5.25% | 3.53 | 10.27% | |
| 30 | PMMA 120 | none | — | 15.5%[b] | 5.69 | 6.98% | |

Notes: [a]All formulations were made and tested as emulsions. Percent active means weight percent tebuconazole in the emulsion.
[b]Although the REA for PMMA 120 without plasticizer was initially high, the release rate thereafter was very low.

EXAMPLE 4

This illustrates the control of the release rate of tebuconazole into water from controlled release microparticles of several different compositions by selection of the matrix polymer and matrix polymer plasticizer and the amount of the plasticizer.

The release rate of tebuconazole was tested for controlled release formulations that were produced in Example 3, test numbers 7, 10, 11 and 30, by mixing an amount of the formulation with water at room temperature so that the total concentration of active ingredient present in the aqueous mixture is no more than about ⅓ of the solubility limit of the active in water at room temperature—about 25° C. The mixture is then mixed in a beaker with a magnetic stirrer. At intervals, aliquots of the mixture are removed and filtered through a 0.45 micron PTFE filter. The amount of the active ingredient in the filtered solution is then measured. For example, when the active ingredient is tebuconazole, about 8 ppm total concentration of tebuconazole was added to the aqueous mixture and the concentration of tebuconazole can be measured by reverse phase HPLC with UV detection.

Figure 3:
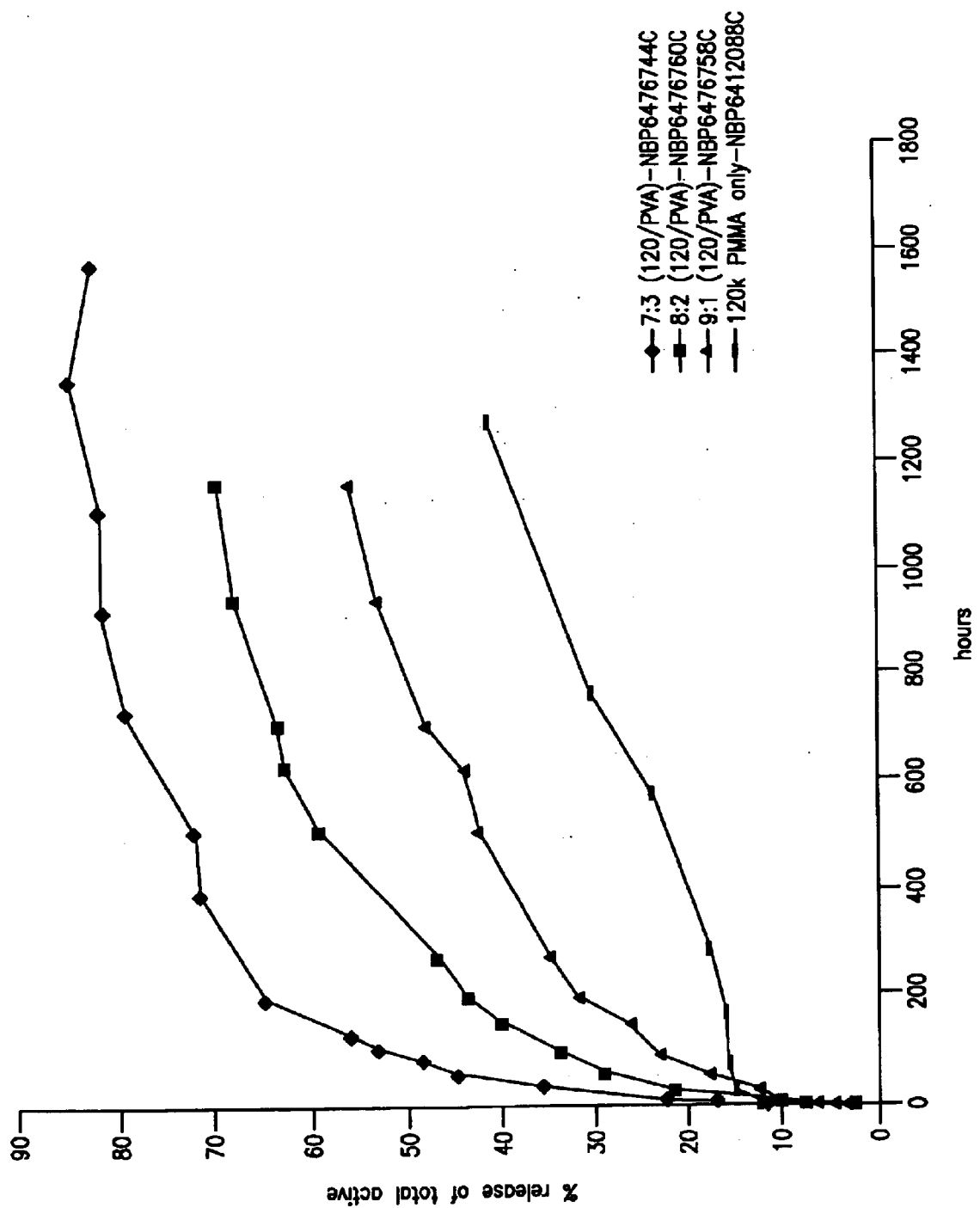

FIG. 3 shows the release rate curves for PMMA alone and for PMMA/PVA blends at different PMMA:PVA ratios. It is seen that the release rate of the tebuconazole was a function of the PMMA:PVA ratio. Thus, it is seen that the release rate of the active could be matched to a selected, or required, release rate by controlling the PMMA:PVA ratio.

Figure 4:
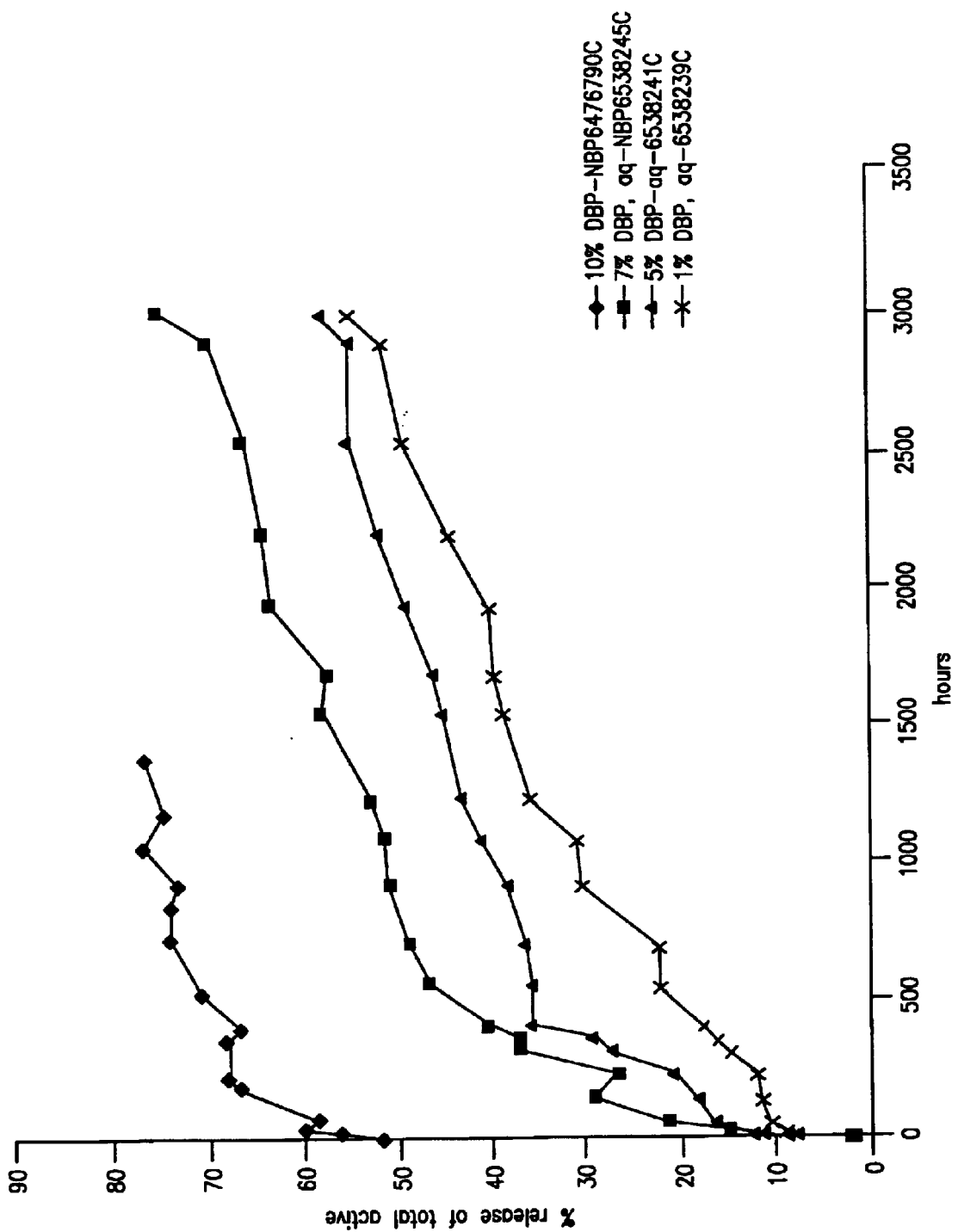
FIG. 4 shows the release rate of tebuconazole into water from matrix microparticles having 40% by weight loading of tebuconazole, with poly(methyl methacrylate) (PMMA) as the matrix polymer and having dibutylphthalate (DBP) as a plasticizer at levels ranging from 1% by weight to 10% by weight; and illustrates the effect that varying the level of plasticizer has on the release rate of the active.

This release rate test was repeated for formulations numbered 22, 23, 26 and 27 of Example 3, which contained PMMA/DBP at ratios from 99:1 to 90:10. The data, shown in FIG. 4, again shows the effect of the MP/MPP ratio upon the release rate of the active.

Figure 5:
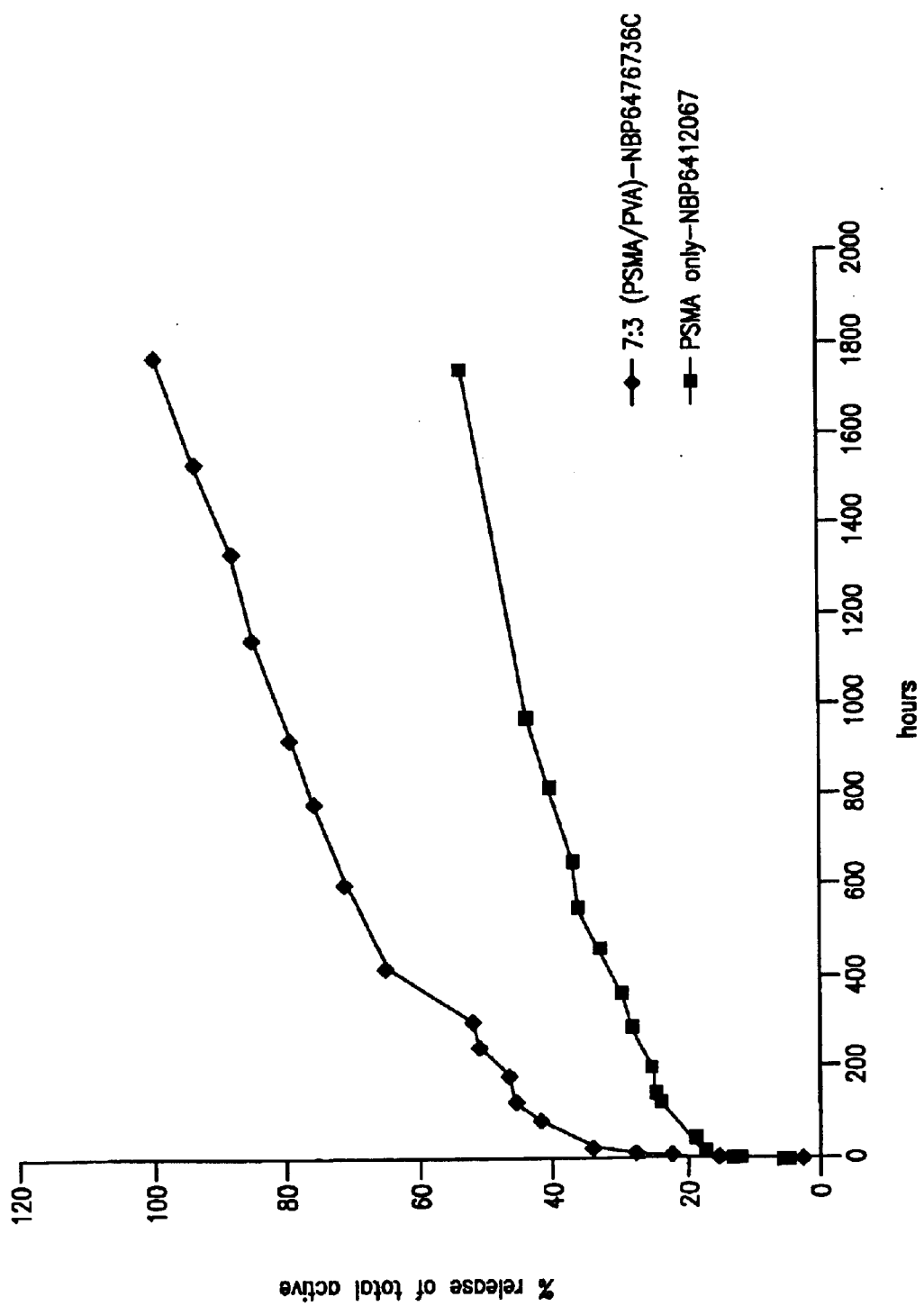
FIG. 5 shows the release rate of tebuconazole into water from matrix microparticles having 40% by weight loading of tebuconazole, with poly(styrene-co-maleic anhydride) (PSMA) as the matrix polymer, without any plasticizer and with and polyvinyl acetate (PVA) as a plasticizer, and illustrates the effect that the addition of plasticizer has on the release rate of the active.

The same release rate test was applied to formulations numbered 13 (PSMA/PVA) and 29 (PSMA) only, to show that poly(styrene-co-maleic anhydride) would also serve as a suitable matrix polymer for tebuconazole. FIG. 5 shows the effect on the release rate of a 70:30 blend of PSMA:PVA as compared to the slower release from PSMA alone.

EXAMPLE 5

This example illustrates the efficacy of controlled release formulations for the protection of wheat from wheat rust.

Spring wheat seeds (Fortuna variety) were planted in sterile Dupo silt loam with Osmacote slow release fertilizer added and a cover layer of 1:1 mixed sterile Dupo silt loam and Metro-mix 200. On the 11th day after planting, controlled release formulations numbered 14 (70:30, PSMA/PVA); 5 (70:30, PMMA 350/PA); and 11 (70:30, PMMA 120/PVA) were injected into the soil alongside the seeds. A control of PMMA/PVA without tebuconazole (MON38412, LUCITE 29), and a commercial preparation of tebuconazole (RAXIL®) were also injected at the same levels as the controlled release formulations. A section of the plants were left untreated as an untreated control (UTC), and another section were treated with a standard commercial foliar spray application of tebuconazole (FOLIAR APPL). All of the controlled release formulations were applied at rates of 100 and 200 g tebuconazole per 100 kg of wheat seed. RAXIL, in furrow and by foliar application, was applied at the standard rate of 100 g AI/100 kg equivalent of seed.

On the 18th day after the injection of the formulations, each wheat plant was inoculated with wheat rust fungus by using in-house rust inoculum being maintained weekly on Caldwell winter wheat. On the tenth day after inoculation, the damage due to wheat rust on the third leaf of each plant was determined by a visual estimation of the area of leaf covered with sporulating lesions. The results, shown in FIG. 6, indicate that RAXIL (in furrow) and the PMMA/PVA without tebuconazole provided a similar low level of protection, as compared with the untreated control. However, each of the three controlled release formulations provided a higher level of protection that the RAXIL, with the protection provided by the 70:30, PSMA/PVA formulation providing the highest level of protection of the controlled release formulations. All three of the controlled release formulations provided a higher level of protection at the higher level of application. The degree of protection provided by 40% tebuconazole in 70:30, PSMA/PVA was almost equal to the protection provided by the foliar application of tebuconazole. This indicates that the controlled release formulations are effective in protecting plant seeds and plants from pest damage to the same, or greater extent than known commercial methods of pest protection.

EXAMPLE 6

This example illustrates the effect on the glass transition temperature of a matrix polymer of intermixing the matrix polymer with a plasticizer.

Samples of 10 to 15 mg of poly(methyl methacrylate) (120,000 weight average molecular weight, Aldrich No. 00123 KF) (PMMA); polyvinyl acetate (Aldrich No. 10925 PR) (PVA); phthalic anhydride (Aldrich No. 04905); a PMMA/phthalic anhydride/tebuconazole controlled release formulation of the present invention (42/18/40 weight ratio); and a PMMA/PVA/tebuconazole formulation of the present invention (48/12/40 weight ratio), were tested for melting point or glass transition temperature ($T_g$, ° C.) in a differential scanning calorimeter. The data is reported in Table 3.

TABLE 3

Glass transition temperature and/or melting point for plasticizers, matrix polymers and controlled release formulations.

| SAMPLE | GLASS TRANSITION TEMPERATURE (° C.) | MELTING POINT (° C.) |
| --- | --- | --- |
| PMMA | 95.95 | — |
| Phthalic anhydride (PA) | — | 136.2 |
| PMMA/PA (70/30 wt. ratio) | 58.1 | |
| PMMA/PA/Tebuconazole (42/18/40 wt. ratio) | 26.58 | 93.36 |
| PVA | 27.12 | — |
| PMMA/PVA/Tebuconazole (48/12/40 wt. ratio) | 25.53 | — |

Figure 7A:
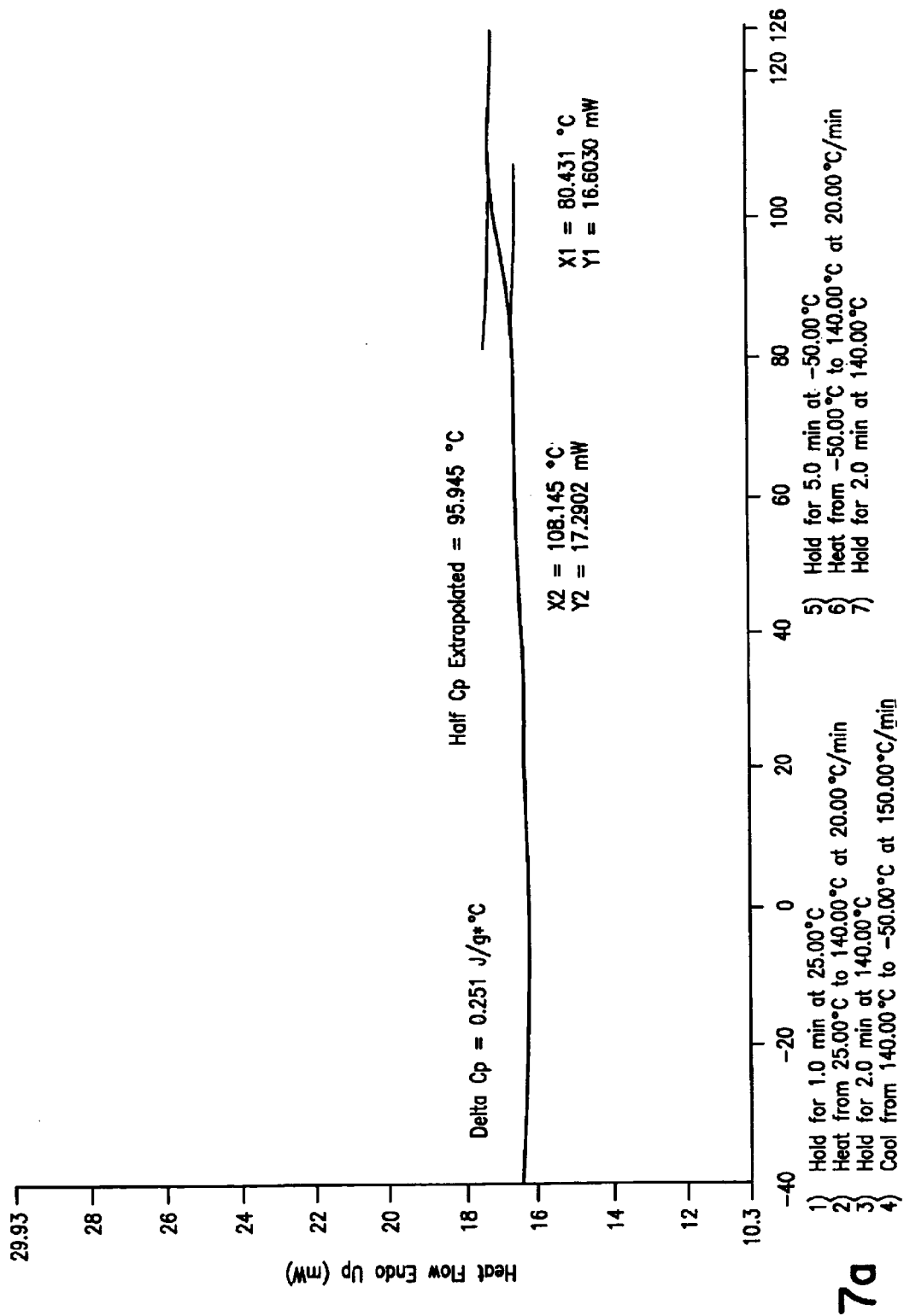
Figure 7B:
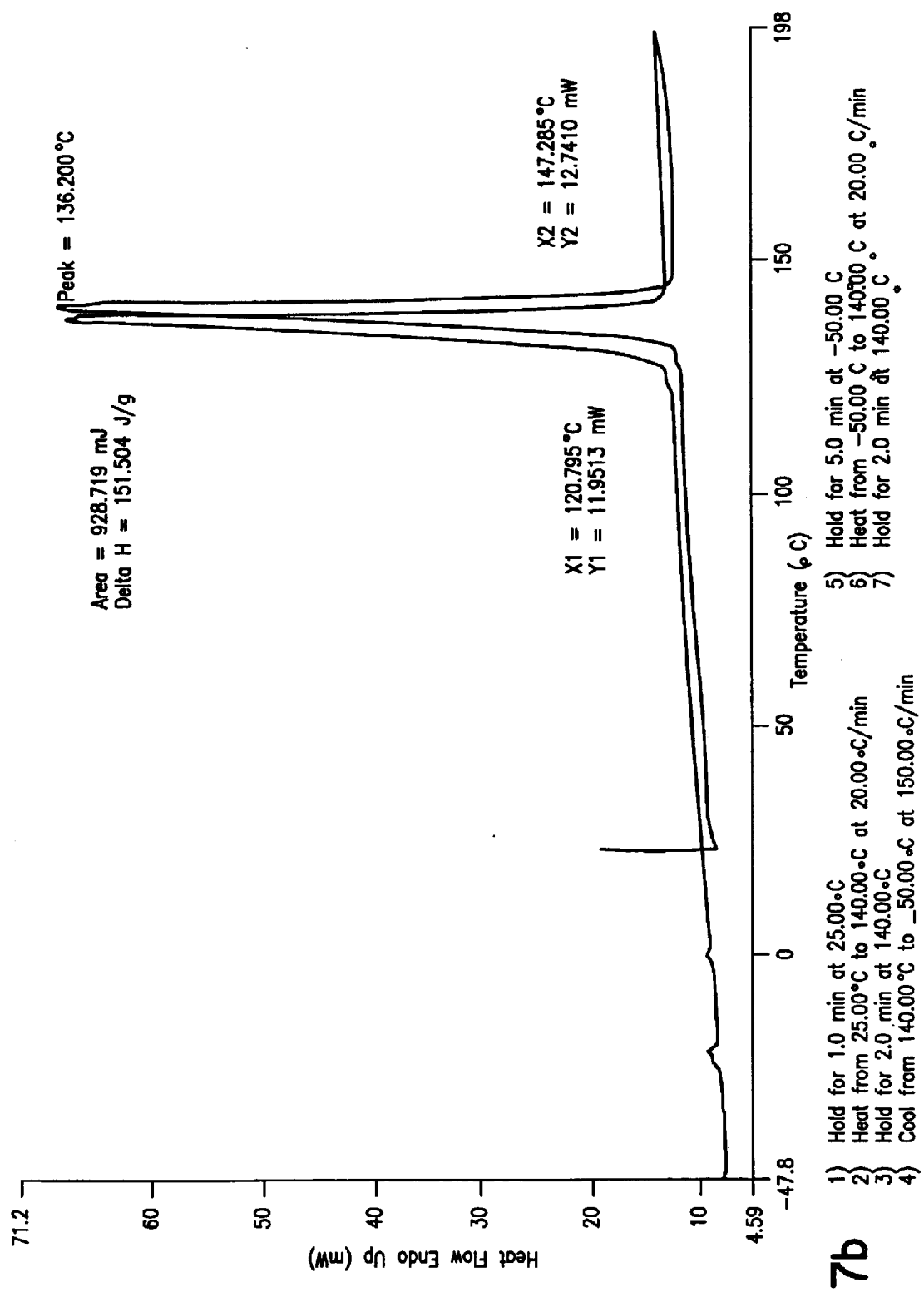
Figure 7C:
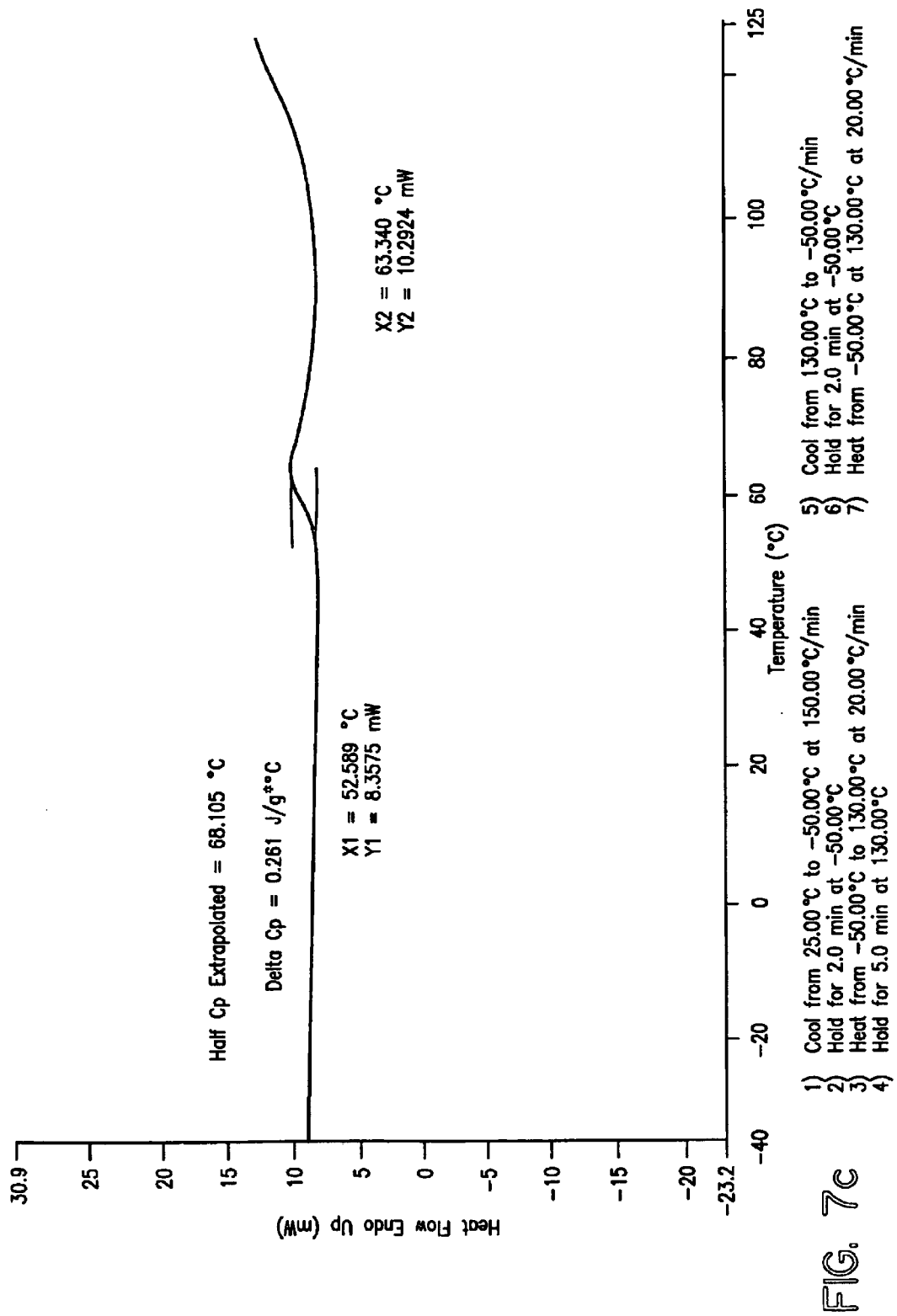
Figure 7D:
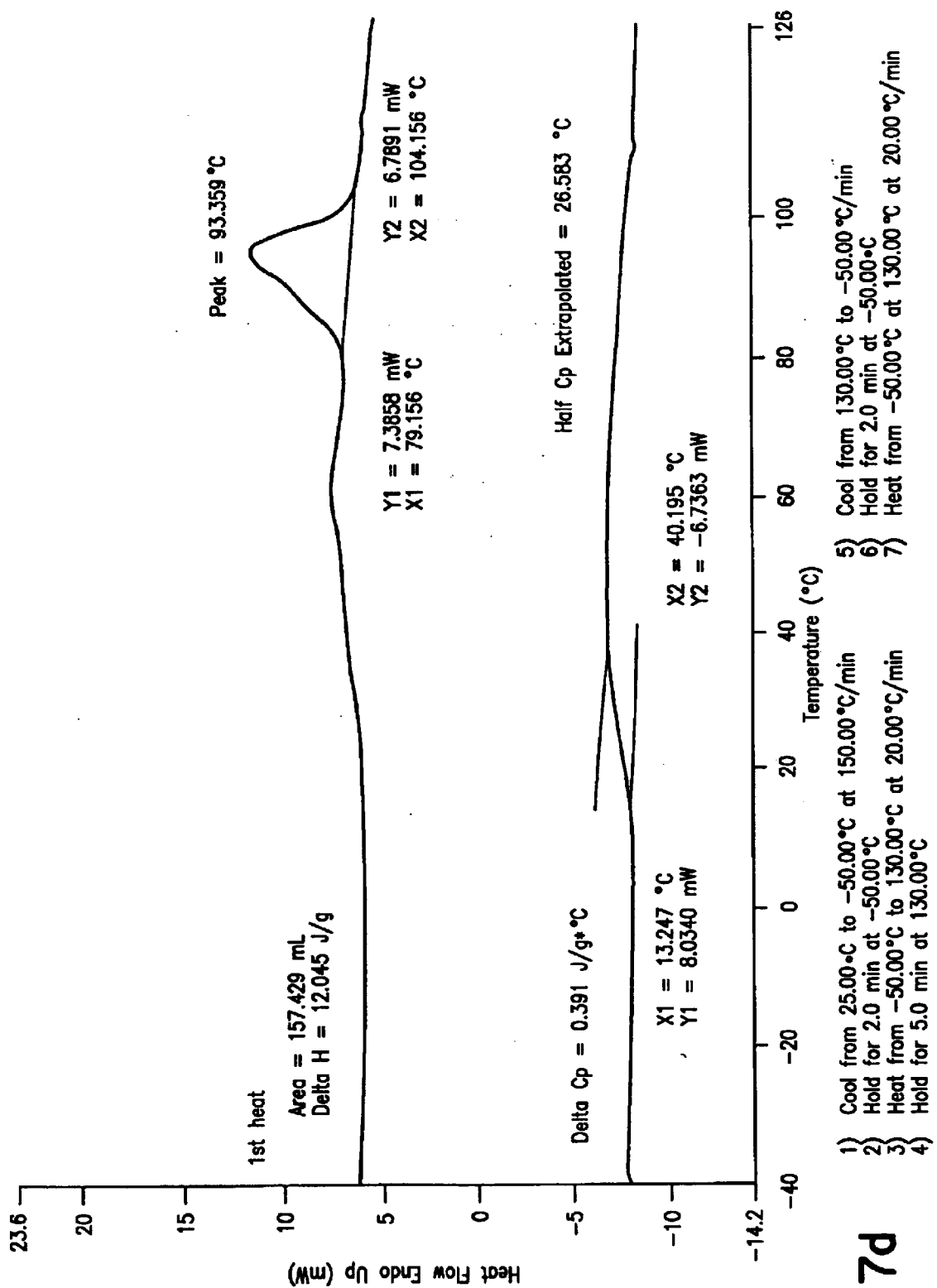

The DSC scans for the first four samples shown in Table 3 are illustrated in FIGS. 7(a)–(c). In this series of four samples, it is seen that the $T_g$ of PMMA alone is about 95.6° C., and that the melting point of PA is about 136° C. The data of the third sample, the mixture of PMMA and PA, shows that intermixing phthalic anhydride with PMMA reduces the $T_g$ of the PMMA to 58° C., or a reduction of almost 40° C. It is believed that this indicates that the PA serves as a plasticizer for the PMMA, and that a PMMA/PA blend would be a useful composition for the present invention. The fourth sample (the 70/30 PMMA/PA blend with sufficient tebuconazole added to make up 40% by weight of the dry preparation) shows a lower $T_g$ of about 26.6° C. This is believed to indicate that the resulting composition should be one having the capability of being modified to match the release rate of the tebuconazole to a pre-selected release rate.

The last two samples shown in Table 3 show the $T_g$ of PVA and the $T_g$ of a PMMA/PVA/tebuconazole blend. Like the previous blend of PMMA/PA/tebuconazole, the blend using PVA shows that this blend should also be useful in the present invention due to the reduced $T_g$ of the blend, compared with that of the PMMA alone. It is believed that this indicates that the PMMA/PVA or the PMMA/phthalic anhydride mixtures would be preferred combinations for use with tebuconazole in the subject controlled release formulations.

All references cited in this specification, including without limitation all papers, publications, presentations, texts, reports, manuscripts, brochures, internet postings, journal articles, periodicals, and the like, are hereby incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A formulation for the controlled release of an azole fungicide comprising an azole fungicide having a solubility in water at 20° C. of less than about 10 g/l dispersed in a matrix polymer that has a reduced glass transition temperature when intermixed with the azole fungicide; and a matrix polymer plasticizer; wherein the ratio of the matrix polymer plasticizer to the matrix polymer is within a range of 1,200.

2. The formulation of claim 1, wherein the azole fungicide is selected from the group consisting of azaconazole, BAS 480F (epoxiconazole), biternatol, bromuconazole, cyproconazole, difenoconazole, diniconazole, fenbuconazole, fluquinconazole, flusilazole, flutriafol, hexaconazole, imazalil, imibenconazole, ipconazole, metconazole, myclobutanil, paclobutrazol, perfuazoate, penconazole, prochloraz, propiconazole, tebuconazole, tetraconazole, triadimefon, triadimenol, triflumizole, triticonazole and uniconazole.

3. The formulation of claim 1 wherein the azole fungicide is tebuconazole.

4. The formulation of claim 1, wherein the matrix polymer is soluble in an organic solvent; is not soluble in water; and is a solid at 25° C.

5. The formulation of claim 4 wherein the matrix polymer has a melting temperature that is not more than 25° C. more than the normal melting point of the azole fungicide.

6. The formulation of claim 5 wherein the matrix polymer has a melting point that is equal to or less than the decomposition temperature of the azole fungicide.

7. The formulation of claim 6 wherein the matrix polymer is totally or partially miscible with the azole fungicide in a molten mixture of the matrix polymer and the azole fungicide.

8. The formulation of claim 4 wherein the matrix polymer is selected from the group consisting of polyesters, polycarbonates and co-polymers of styrene.

9. The formulation of claim 4 wherein the matrix polymer is selected from the group consisting of acrylonitrile-butadiene-styrene terpolymer (ABS); ABS modified polyvinylchloride; ABS-polycarbonate blends; acrylic resins and copolymers; poly(methacrylate), poly(ethylmethacrylate), poly(methylmethacrylate), methylmethacrylate or ethylmethacrylate copolymers with other unsaturated monomers; casein; cellulosic polymers: ethyl cellulose, cellulose acetate, cellulose acetatebutyrate; ethyl vinyl acetate polymers and copolymers; poly(ethylene glycol); poly(vinylpyrrolidone); acetylated mono-, di-, and tri-glycerides; poly(phosphazene); chlorinated natural rubber; polybutadiene; polyurethane; vinylidene chloride polymers and copolymers; styrene-butadiene copolymers; styrene-acrylic copolymers; alkylvinylether polymers and copolymers; cellulose acetate phthalates; epoxies; ethylene copolymers: ethylene-vinyl acetate-methacrylic acid, ethylene-acrylic acid copolymers; methylpentene polymers; modified phenylene oxides; polyamides; melamine formaldehydes; phenolformaldehydes; phenolic resins; poly(orthoesters); poly(cyanoacrylates); polydioxanone; polycarbonates; polyesters; polystyrene; polystyrene copolymers: poly(styrene-co maleic anhydride); urea-formaldehyde; urethanes; vinyl resins: vinyl chloride-vinyl acetate copolymers, polyvinyl chloride; biodegradable polyesters; starch-polyester alloys; styrene-maleic anhydride copolymers; poly(methylvinyl ether-maleic acid); starch; starch-PCL blends; polylactic acid (PLA)-starch blends; polylactic acid; poly(lactic acid-glycolic acid) copolymers; PCL; cellulose esters; cellulose acetate butyrate; starch esters; starch ester-aliphatic polyester blends; modified corn starch; polycaprolactone; poly(n-amylmethacrylate); ethyl cellulose; wood rosin; polyanhydrides; polyvinylalcohol (PVOH); polyhydroxybutyrate-valerate (PHBV); biodegradable aliphatic polyesters; polyhydroxybutyrate (PHB); biodegradable aliphatic polyesters (BIONOLLE); and mixtures of two or more of these.

10. The formulation of claim 9 wherein the matrix polymer is selected from the group consisting of poly(methylmethacrylate) and poly(styrene-co maleic anhydride).

11. The formulation of claim 10 wherein the matrix polymer is poly(methylmethacrylate).

12. The formulation of claim 11 wherein the poly(methylmethacrylate) has a weight average molecular weight of from about 100,000 to about 400,000.

13. The formulation of claim 12 wherein the poly(methylmethacrylate) has a weight average molecular weight of from about 120,000.

14. The formulation of claim 2 wherein the matrix polymer is poly(methylmethacrylate) having a weight average molecular weight of from about 100,000 to about 400,000.

15. The formulation of claim 14 wherein the poly(methylmethacrylate) has a weight average molecular weight of from about 120,000.

16. The formulation of claim 4 wherein the matrix polymer plasticizer is totally or partially miscible with the matrix polymer at 25° C. and has a plasticizing effect upon the matrix polymer when intermixed with the matrix polymer.

17. The formulation of claim 16 wherein the matrix polymer plasticizer is selected from the group consisting of: high-boiling esters of polybasic acids; phosphoric acids; phosphorous acids; phosphonic acids; substituted fatty acids; high-boiling glycols; polyglycols; polyoxyalkylenes and glycerol each optionally substituted and optionally terminally esterified; pentaerythritols; sulphonic acids; expoxies; chlorinated paraffins; block copolyesters; block polyester copolyethers; polymeric esters; and mixtures thereof.

18. The formulation of claim 17 wherein the matrix polymer plasticizer is selected from the group consisting of:

(A) high boiling esters of polybasic acids:

(i) phthalates and isophthalates, having the formula:

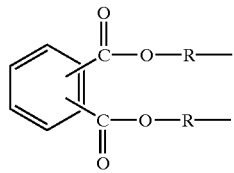

where $R_1$ is $C_{1-20}$ alkyl, cycloalkyl or benzyl, $C_{5-11}$ alkyl, cyclohexyl or benzyl, isoheptyl, isoocytl, isononyl, isodecyl and isoundecyl;

(ii) citrates; doubly esterified hydroxycarboxylic acids having at least 3 ester groups in its molecule, acetyl tri-n-butyl citrate; citrates of the formula:

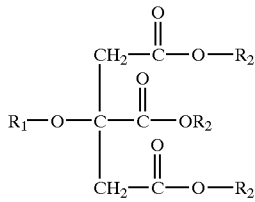

where $R_1$ is hydrogen or $C_{1-10}$ alkyl, and $R_2$ is $C_{1-10}$ alkyl, $C_{1-10}$ alkoxy or $C_{1-10}$ alkoxyalkyl; when $R_1$ and $R_2$ are alkyl each is straight or branched chain, methyl, ethyl, propyl, butyl, pentyl, hexyl, iso-propyl, isobutyl, or ethoxyethyl, propoxyathyl, butoxyethyl, butoxy, isopropyl and butoxyethoxyethyl;

(iii) fumarates;

(iv) glutarates; diester ether alkyl;

(v) adipates, having the formula $R_1$—O—C(O)—(CH$_2$)$_4$— C(O)—OR$_2$ where $R_1$ and $R_2$ which may be the same or different and are $C_{2-12}$ alkyl, $C_{2-12}$ alkoxyalkyl; di-2-ethylhexyl adipate, di-isodecyl adipate, di-isononyl adipate, dioctyl adipate;

(vi) sebacates of the formula $R_1$—O—C(O)—(CH$_2$)$_8$—C(O)—O—$R_1$ where $R_1$ is $C_{2-15}$ alkyl or $C_{2-15}$ alkoxyalkyl; di-octyl sebacate, di-dodecyl sebacate, di-butoxyethyl sebacate, or di-n-butyl sebacate;

(ix) azelates of the formula $R_1$—O—C(O)—(CH$_2$)$_7$—C(O)—$R_1$ where $R_1$ is $C_{2-12}$, alkyl, benzyl, or $C_{2-12}$ alkoxy-alkyl, for example, di-n-butyl azelate and di i-octyl azelate;

(B) high-boiling glycols, polyglycols, polyoxyalkylenes and glycerol:

(i) high molecular weight glycols, triethylene glycol diacetate, triethylene glycol caprylate, alkyl ethers/esters of general formula $R_2$—(O—CH$_2$—CH$_2$)$_n$—O—$R_1$ where $R_1$ is alkyl or —C(O)-alkyl, $R_2$ is alkyl and n is 2 to 100;

(ii) polyglycols; poly(propylene glycol), poly(ethylene) glycol;

(iii) glycerols glycerol tricaprolate, glycerol tributyrate;

(iv) pentaerythritols;

(C) sulphonic acids; toluenesulphonamide;

(D) epoxy derivatives of the formula CH$_3$—(CH$_2$)$_n$-A-(CH$_2$)$_n$—R in which the A is an alkene containing one or more double bonds, n is up to 25 and R is $C_{2-15}$ alkyl, or epoxy derivatives of triglycerides containing one or more double bonds per fatty acid chain with chain lengths from $C_{6-26}$;

(E) substituted fatty acids, palmitates, stearates, oleates, ricinoleates and laurates, sorbitan monolaurate, sorbitan monooleate, poly(oxyethylene), sorbitan monolaurate), poly(oxyethylene)(4)lauryl ether, butyl acetyl ricinoleate;

(F) phosphoric acid derivatives (phosphates), compounds of the formula O=P(OR)$_3$ where R is straight chain or branched $C_{1-25}$ alkyl, alkoxyalkyl, phenyl, or phenylalkyl where the alkyl is straight chain or branched $C_{1-25}$; isopropyl phenyl phosphate; phosphonic acids; phosphites;

(G) chlorinated paraffins;

(H) polymeric esters of the formula —O—C(O)—$R_1$—C(O)—O—$R_2$—O— in which $R_1$ and $R_2$ are both independently $C_{2-12}$ alkylene, $R_2$ is derived from a diol such as 1,2-propanediol, 1,3 butanediol, 1,4-butanediol or 1,6-hexanediol;

(i) polyester glutarates having molecular weights from 2000 to 20,000;

(ii) polyester adipates having a molecular weight from 200 to 20000, poly(propylene) adipate, poly(1,3-butylene glycol-co-1,2-propylene glycol adipic acid) terminated with 2-ethylhexanol, poly(neopentyl glycol-co-1,4-butylene glycol adipic acid) terminated with 2-ethylhexanol, poly(1,3-butylene glycol adipic acid) unterminated, poly(1,3-butylene glycol adipic acid) unterminated, poly(1,2-propylene glycol 5 adipic acid-co-phthalic acid) terminated with 2-ethylhexanol, poly (neopentyl glycol adipic acid) terminated with 2ethylhexanol, poly(1,2propylene glycol adipic acid-co-phthalic acid) terminated with 2-ethylhexanol, poly (1,2-propylene glycol-co-1,4-butylene glycol adipic acid) terminated with 2 ethylhexanol, poly (1,3-butylene glycol adipic acid) terminated with mixed fatty acids, poly(1,2propylene glycol adipic acid) terminated with 2-ethylhexanol, poly(1,2-propylene glycol-co-1,4-butylene glycol adipic acid) terminated with 2-ethylhexanol, poly(1,4-butylene glycol adipic acid), or poly(1,4-butylene glycol-co ethylene glycol adipic acid);

(iii) succinic polyesters;

(iv) sebacic polyesters having a molecular weight from 4000 to 10000, (v) lactone copolymers of the formula [—(O—C(O)—$R_1$—C(O)—O—$R_2$—O)]$_m$[—C(O)—$R_3$—O—]$_n$, where $R_1$ and $R_2$ both independently $C_{2-12}$ alkylene, or $R_2$ may be derived from a diol selected from 1,2-propanediol, 1,3-butanediol, 1,4-butanediol or 1,6-hexanediol, and $R_3$ is —(CH$_2$)$_5$-(based on caprolactone);

(vi) polyesters (esters of mixed adipic, glutaric and succinic acids with isodecanol), polycaprolactone triol;

(I) and mixtures of two or more of these.

19. The formulation of claim 17 wherein the matrix polymer plasticizer is selected from the group consisting of phthalic anhydride, poly(vinyl acetate) and dibutyl phthalate.

20. The formulation of claim 15 wherein the matrix polymer plasticizer is selected from the group consisting of phthalic anhydride, poly(vinyl acetate) and dibutyl phthalate.

21. The formulation of claim 20 wherein the matrix polymer plasticizer is poly(vinyl acetate) or dibutyl phthalate.

22. The formulation of claim 1 wherein the amount of readily extractable active ingredient (REA) in an excess of water at 25° C. is less than 25% of the total azole fungicide in the formulation.

23. The formulation of claim 22 wherein the amount of readily extractable active ingredient (REA) in an excess of water at 25° C. is less than 15% of the total azole fungicide in the formulation.

24. The formulation of claim 23 wherein the amount of readily extractable active ingredient (REA) in an excess of water at 25° C. is less than 10% of the total azole fungicide in the formulation.

25. The formulation of claim 24 wherein the amount of readily extractable active ingredient (REA) in an excess of water at 25° C. is less than 5% of the total azole fungicide in the formulation.

26. The formulation of claim 20 wherein the amount of readily extractable active ingredient (REA) in an excess of water at 25° C. is less than 15% of the total azole fungicide in the formulation.

27. The formulation of claim 1 in the form of microparticles having an average size of 100 microns or less.

28. The formulation of claim 27 in the form of microparticles having an average size of 50 microns or less.

29. The formulation of claim 28 in the form of microparticles having an average size of 20 microns or less.

30. The formulation of claim 26 in the form of microparticles wherein 80% of the particles have a size of 100 microns or less.

31. The formulation of claim 30 wherein 80% of the particles have a size of 20 microns or less.

32. The formulation of claim 26 wherein the formulation is in the form of microparticles and wherein 80% of the particles have a size of 20 microns or less.

33. The formulation of claim 1 wherein the amount of azole fungicide is between about 1% and about 60% by weight of the formulation.

34. The formulation of claim 33 wherein the amount of azole fungicide is at least about 5% by weight of the formulation.

35. The formulation of claim 34 wherein the amount of azole fungicide is at least about 10% by weight of the formulation.

36. The formulation of claim 35 wherein the amount of azole fungicide is at least about 20% by weight of the formulation.

37. The formulation of claim 36 wherein the amount of azole fungicide is at least about 30% by weight of the formulation.

38. The formulation of claim 30 wherein the azole fungicide comprises tebuconazole and the amount of tebuconazole is at least about 3% by weight of the formulation.

39. The formulation of claim 35 wherein the microparticles are dispersed in a carrier liquid.

40. The formulation of claim 39 wherein the carrier liquid is water.

41. A method of administering an azole fungicide to seeds by treating the seeds with the formulation of claim 1.

42. The method of claim 41 wherein the formulation comprises microparticles that are applied as a coating.

43. A method of administering a pesticide to a plant by treating the plant with the formulation of claim 1.

44. The method of claim 43 wherein the formulation is administered to the plant by spraying.

45. A seed that has been treated with the formulation of claim 1.

46. The seed of claim 45 wherein the seed is a seed of a plant selected from the group consisting of corn, peanut, canola/rapeseed, soybean, curcubits, crucifers, cotton, rice, sorghum, sugar beet, wheat, barley, rye, sunflower, tomato, sugarcane, tobacco, oats, vegetables, and leaf crops.

47. The seed of claim 46 wherein the seed is a seed of a transgenic plant.

48. A plant that has been treated with the formulation of claim 1.

49. The plant of claim 48 wherein the plant is a transgenic plant.

50. The method according to claim 30, comprising the step of selecting a release rate for the azole fungicide before selecting the matrix polymer.

51. A controlled release formulation comprising tebuconazole in an amount of about 30% to 40% by weight, and poly(methyl methacylate) and phthalic anhydride or poly (vinyl acetate) in a weight ratio of from about 90:10 to 50:50.

52. A controlled release formulation comprising tebuconazole in an amount of about 30% to 40% by weight, and poly(styrene-co-maleic anhydride) and poly(vinyl acetate) in a weight ratio of from about 90:10 to 50:50.

53. A method of making a formulation for the controlled release of an azole fungicide having a solubility in water at 20° C. of less than about 10 g/l comprising intermixing an azole fungicide and a matrix polymer with a sufficient amount of a matrix polymer plasticizer; wherein the ratio of the matrix polymer plasticizer to the matrix polymer is within a range of 1,200 to about 1,1.5 wt/wt to provide a formulation having a release rate for the azole fungicide that matches a selected release rate.

54. The method of claim 53, wherein the azole fungicide is selected from the group consisting of azaconazole, BAS 480F (epoxiconazole), biternatol, bromuconazole, cyproconazole, difenoconazole, diniconazole, fenbuconazole, fluquinconazole, flusilazole, flutnafol, hexaconazole, imazalil, imibenconazole, ipconazole, metconazole, myclobutanil, paclobutrazol, perfuazoate, penconazole, prochloraz, propiconazole, tebuconazole, tetraconazole, triadimefon, triadimenol, triflumizole, tritiiconazole and uniconazole.

55. The method of claim 54 wherein the matrix polymer is selected from the group consisting of acrylonitrilebutadiene-styrene terpolymer (ABS); ABS modified polyvinylchloride; ABS-polycarbonate blends; acrylic resins and copolymers; poly(methacrylate), poly(ethylmethacrylate), poly(methylmethacrylate), methylmethacrylate or ethylmethacrylate copolymers with other unsaturated monomers; casein; cellulosic polymers: ethyl cellulose, cellulose acetate, cellulose acetatebutyrate; ethyl vinyl acetate polymers and copolymers; poly(ethylene glycol); poly (vinylpyrrolidone); acetylated mono-, di-, and tri-glycerides; poly(phosphazene); chlorinated natural rubber; polybutadiene; polyurethane; vinylidene chloride polymers and copolymers; styrene-butadiene copolymers; styrene-acrylic copolymers; alkylvinylether polymers and copolymers; cellulose acetate phthalates; epoxies; ethylene copolymers: ethylene-vinyl acetate-methacrylic acid, ethylene-acrylic acid copolymers; methylpentene polymers; modified phenylene oxides; polyamides; melamine formaldehydes; phenolformaldehydes; phenolic resins; poly(orthoesters); poly (cyanoacrylates); polydioxanone; polycarbonates; polyesters; polystyrene; polystyrene copolymers: poly (styrene-co maleic anhydride); urea-formaldehyde; urethanes; vinyl resins: vinyl chloride-vinyl acetate copolymers, polyvinyl chloride; biodegradable polyesters; starch-polyester alloys; styrene-maleic anhydride copolymers; poly(methylvinyl ether-maleic acid); starch; starch- PCL blends; polylactic acid (PLA)-starch blends; polylactic acid; poly(lactic acid-glycolic acid) copolymers; PCL; cellulose esters; cellulose acetate butyrate; starch esters; starch ester-aliphatic polyester blends; modified corn starch; polycaprolactone; poly(n-amylmethacrylate); ethyl cellulose; wood rosin; polyanhydrides; polyvinylalcohol (PVOH); polyhydroxybutyrate-valerate (PHBV); biodegradable aliphatic polyesters; polyhydroxybutyrate (PHB); biodegradable aliphatic polyesters (BIONOLLE); and mixtures of two or more of these.

56. The method of claim 54 wherein the matrix polymer plasticizer is selected from the group consisting of:

(A) high boiling esters of polybasic acids:
(i) phthalates and isophthalates, having the formula:

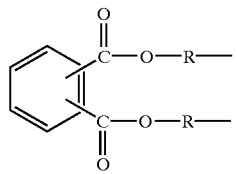

where $R_1$ is $C_{1-20}$ alkyl, cycloalkyl or benzyl, $C_{5-11}$ alkyl, cyclohexyl or benzyl, isoheptyl, isoocytl, isononyl, isodecyl and isoundecyl;

(ii) citrates; doubly esterified hydroxycarboxylic acids having at least 3 ester groups in its molecule, acetyl tri-n-butyl citrate; citrates of the formula:

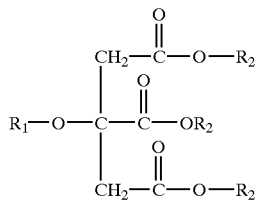

where $R_1$ is hydrogen or $C_{1-10}$ alkyl, and $R_2$ is $C_{1-10}$ alkyl, $C_{1-10}$ alkoxy or $C_{1-10}$ alkoxyalkyl; when $R_1$ and $R_2$ are alkyl each is straight or branched chain, methyl, ethyl, propyl, butyl, pentyl, hexyl, iso-propyl, isobutyl, or ethoxyethyl, propoxyethyl, butoxyethyl, butoxy, iso-propyl and butoxyethoxyethyl;

(iii) fumarates;
(iv) glutarates; diester ether alkyl;
(v) adipates, having the formula $R_1$—O—C(O)—$(CH_2)_4$—C(O)—$OR_2$ where $R_1$ and $R_2$ which may be the same or different and are $C_{2-12}$ alkyl, $C_{2-12}$ alkoxyalkyl; di-2-ethylhexyl adipate, di-isodecyl adipate, di-isononyl adipate, dioctyl adipate;
(vi) sebacates of the formula $R_1$—O—C(O)—$(CH_2)_8$—C(O)—O—$R_1$ where $R_1$ is $C_{2-15}$ alkyl or $C_{2-15}$ alkoxyalkyl; di-octyl sebacate, di-dodecyl sebacate, di-butoxyethyl sebacate, or di-n-butyl sebacate;
(ix) azelates of the formula $R_1$—O—C(O)—$(CH_2)_7$—C(O)—$R_1$ where $R_1$ is $C_{2-12}$, alkyl, benzyl, or $C_{2-12}$ alkoxy-alkyl, for example, di-n-butyl azelate and di i-octyl azelate;

(B) high-boiling glycols, polyglycols, polyoxyalkylenes and glycerol:
(i) high molecular weight glycols, triethylene glycol diacetate, triethylene glycol caprylate, alkyl ethers/esters of general formula $R_2$—(O—$CH_2$—$CH_2$)$_n$—O—$R_1$ where $R_1$ is alkyl or —C(O)-alkyl, $R_2$ is alkyl and n is 2 to 100;
(ii) polyglycols; poly(propylene glycol), poly(ethylene) glycol;
(iii) glycerols glycerol tricaprolate, glycerol tributyrate;
(iv) pentaerythritols;

(C) sulphonic acids; toluenesulphonamide;

(D) epoxy derivatives of the formula $CH_3$—$(CH_2)_n$-A-$(CH_2)_n$—R in which the A is an alkene containing one or more double bonds, n is up to 25 and R is $C_{2-15}$ alkyl, or epoxy derivatives of triglycerides containing one or more double bonds per fatty acid chain with chain lengths from $C_{6-26}$;

(E) substituted fatty acids, palmitates, stearates, oleates, ricinoleates and laurates, sorbitan monolaurate, sorbitan monooleate, poly(oxyethylene), sorbitan monolaurate), poly(oxyethylene)(4)lauryl ether, butyl acetyl ricinoleate;

(F) phosphoric acids (phosphates), compounds of the formula $O=P(OR)_3$ where R is straight chain or branched $C_{1-25}$ alkyl, alkoxyalkyl, phenyl, or phenylalkyl where the alkyl is straight chain or branched $C_{1-25}$; isopropyl phenyl phosphate; phosphonic acids; phosphites;

(G) chlorinated paraffins;

(H) polymeric esters of the formula —O—C(O)—$R_1$—C(O)—O—$R_2$—O— in which $R_1$ and $R_2$ are both independently $C_{2-12}$ alkylene, $R_2$ is derived from a diol such as 1,2-propanediol, 1,3 butanediol, 1,4-butanediol or 1,6-hexanediol;
(i) polyester glutarates having molecular weights from 2000 to 20,000;
(ii) polyester adipates having a molecular weight from 200 to 20000, poly(propylene) adipate, poly(1,3-butylene glycol-co-1,2-propylene glycol adipic acid) terminated with 2-ethylhexanol, poly(neopentyl glycol-co-1,4-butylene glycol adipic acid) terminated with 2-ethylhexanol, poly(1,3-butylene glycol adipic acid) unterminated, poly(1,3-butylene glycol adipic acid) unterminated, poly(1,2-propylene glycol 5 adipic acid-co-phthalic acid) terminated with 2-ethylhexanol, poly (neopentyl glycol adipic acid) terminated with 2ethylhexanol, poly(1,2propylene glycol adipic acid-co-phthalic acid) terminated with 2-ethylhexanol, poly (1,2-propylene glycol-co-1,4-butylene glycol adipic acid) terminated with 2 ethylhexanol, poly (1,3-butylene glycol adipic acid) terminated with mixed fatty acids, poly(1,2 propylene glycol adipic acid) terminated with 2-ethylhexanol, poly(1,2-propylene glycol-co-1,4-butylene glycol adipic acid) terminated with 2-ethylhexanol, poly(1,4-butylene glycol adipic acid), or poly(1,4-butylene glycol-co ethylene glycol adipic acid);
(iii) succinic polyesters;
(iv) sebacic polyesters having a molecular weight from 4000 to 10000,
(v) lactone copolymers of the formula [—(O—C(O)—$R_1$—C(O)—O—$R_2$—O)]$_m$[—C(O)—$R_3$—O—]$_n$, where $R_1$ and $R_2$ are both independently $C_{2-12}$ alkylene, or $R_2$ may be derived from a diol selected from 1,2-propanediol, 1,3-butanediol, 1,4-butanediol or 1,6-hexanediol, and $R_3$ is —$(CH_2)_5$-(based on caprolactone);
(vi) polyesters (esters of mixed adipic, glutaric and succinic acids with isodecanol), polycaprolactone triol;

(I) WOLFLEX-BUT; and mixtures of two or more of these.

57. The method of claim 53, wherein the method comprises the steps of:
   (a) dissolving a matrix polymer in an organic solvent;
   (b) dissolving or dispersing an active ingredient and a matrix polymer plasticizer in the same organic solvent with the matrix polymer to make an organic mixture;
   (d) mixing the organic mixture with water that contains at least one surfactant to form microparticles of the formulation in an organic/water emulsion; and
   (e) removing the organic solvent from the organic/water emulsion; wherein a sufficient amount of the matrix polymer plasticizer is added to provide a formulation having a release rate for the active ingredient that matches a selected release rate.

58. The method of claim 53 wherein the method comprises the steps of:
   (a) intermixing a matrix polymer with an active ingredient and a matrix polymer plasticizer in a molten state to form a melt; and
   (b) forming microparticles of the formulation from the melt; wherein a sufficient amount of the matrix polymer plasticizer is added to provide a formulation having a release rate for the active ingredient that matches a selected release rate.

59. The method of claim 58 wherein the microparticles are formed prior to solidification of the melt.

60. The method of claim 58 wherein the melt is solidified and microparticles are formed by size reduction of the solidified formulation.

61. A method of making a formulation for the controlled release of an azole fungicide comprising:
   selecting a matrix polymer having a glass transition temperature that is reduced when the matrix polymer is intermixed with the azole fungicide having a solubility in water at 20° C. of less than about 10 g/l;
   intermixing the azole fungicide and the matrix polymer with a sufficient amount of a matrix polymer plasticizer to provide a formulation having a release rate for the azole fungicide that matches a selected release rate; the ratio of the matrix polymer plasticizer to the matrix polymer is within a range 1,200 to about 1,1.5 wt/wt.

* * * * *

UNITED STATES PATENT AND TRADEMARK OFFICE
CERTIFICATE OF CORRECTION

PATENT NO.   : 6,858,634 B2
DATED        : February 22, 2005
INVENTOR(S)  : Jawed Asrar and James F. Essinger, Jr.

It is certified that error appears in the above-identified patent and that said Letters Patent is hereby corrected as shown below:

Column 2,
Line 67, replace the term "partices" with the term -- particles --.

Column 3,
Line 34, insert the term -- be -- between the terms "would" and "advantages", Column 5,
Line 27, delete the term "and" between the terms "with" and "polyvinyl".

Column 7,
Line 49, insert the term -- in -- between the terms "is" and "contact".
Line 67, replace the term "that" with the term -- than --.

Column 8,
Line 54, insert the term -- it -- between the terms "if" and "is"

Column 10,
Line 55, replace the term "IS" with the term -- is --.

Column 16,
Line 18, replace the term "and" with the term -- an --.

Column 20,
Line 36, replace the term "convention" with the term -- conventional --.
Line 49, insert the punctuation -- . -- after term "formulation".
Line 52, replace the term "conventional" with the term "conventionally".

Column 22,
Line 16, insert the term -- of -- between the terms "use" and "several".

Column 27,
Line 16, replace the term "art.Applicants" with the terms -- art. Applicants --.

UNITED STATES PATENT AND TRADEMARK OFFICE
CERTIFICATE OF CORRECTION

PATENT NO.  : 6,858,634 B2
DATED       : February 22, 2005
INVENTOR(S) : Jawed Asrar and James F. Essinger, Jr.

It is certified that error appears in the above-identified patent and that said Letters Patent is hereby corrected as shown below:

Column 29,
Line 31, replace the term "propoxyathyl" with the term -- propoxyethyl --.

Column 32,
Line 35, replace the term "flutnafol" with the term -- flutriafol --.

Signed and Sealed this

Nineteenth Day of July, 2005

JON W. DUDAS
*Director of the United States Patent and Trademark Office*